(12) United States Patent
Altman et al.

(10) Patent No.: US 8,987,456 B2
(45) Date of Patent: Mar. 24, 2015

(54) 3-PYRIDYL CARBOXAMIDE-CONTAINING SPLEEN TYROSINE KINASE (SYK) INHIBITORS

(71) Applicant: Merck Sharp & Dohme Corp., Rahway, NJ (US)

(72) Inventors: Michael D. Altman, Needham, MA (US); Kaleen Konrad Childers, Newton, MA (US); Anthony Donofrio, Cambridge, MA (US); John Michael Ellis, Needham, MA (US); Sandra Lee Knowles, Princeton, NJ (US); Alan B. Northrup, Reading, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/349,563

(22) PCT Filed: Oct. 1, 2012

(86) PCT No.: PCT/US2012/058218
§ 371 (c)(1),
(2) Date: Apr. 3, 2014

(87) PCT Pub. No.: WO2013/052393
PCT Pub. Date: Apr. 11, 2013

(65) Prior Publication Data
US 2014/0303206 A1 Oct. 9, 2014

Related U.S. Application Data

(60) Provisional application No. 61/543,545, filed on Oct. 5, 2011.

(51) Int. Cl.
| | |
|---|---|
| *C07D 215/38* | (2006.01) |
| *C07D 401/12* | (2006.01) |
| *C07D 401/14* | (2006.01) |
| *C07D 405/14* | (2006.01) |
| *A61K 31/444* | (2006.01) |
| *A61K 31/4709* | (2006.01) |

(52) U.S. Cl.
CPC ............ *C07D 401/12* (2013.01); *C07D 401/14* (2013.01); *C07D 405/14* (2013.01); *A61K 31/444* (2013.01); *A61K 31/4709* (2013.01)
USPC .......................................... 546/159; 514/312

(58) Field of Classification Search
USPC .......................................... 546/159; 514/312
See application file for complete search history.

(56) References Cited

U.S. PATENT DOCUMENTS

| | | |
|---|---|---|
| 5,710,129 A | 1/1998 | Lynch et al. |
| 6,248,790 B1 | 6/2001 | Uckun et al. |
| 6,432,963 B1 | 8/2002 | Hisamichi et al. |
| 6,589,950 B1 | 7/2003 | Collingwood et al. |
| 6,770,643 B2 | 8/2004 | Cox et al. |
| 6,797,706 B1 | 9/2004 | Hisamichi et al. |
| 6,897,207 B2 | 5/2005 | Cox et al. |
| 6,897,208 B2 | 5/2005 | Edwards et al. |
| 6,911,443 B2 | 6/2005 | Yura et al. |
| 7,060,827 B2 | 6/2006 | Singh et al. |
| 7,122,542 B2 | 10/2006 | Singh et al. |
| 7,227,020 B2 | 6/2007 | Cox et al. |
| 7,259,154 B2 | 8/2007 | Cox et al. |
| 7,276,502 B2 | 10/2007 | Brenchley et al. |
| 8,367,658 B2 * | 2/2013 | Collins et al. ............ 514/217.05 |
| 2004/0029902 A1 | 2/2004 | Singh et al. |
| 2004/0054179 A1 | 3/2004 | Yura et al. |
| 2006/0135543 A1 | 6/2006 | Singh et al. |
| 2006/0178407 A1 | 8/2006 | Argade et al. |
| 2006/0205731 A1 | 9/2006 | Kodama et al. |
| 2006/0211657 A1 | 9/2006 | Singh et al. |
| 2006/0234483 A1 | 10/2006 | Arak et al. |
| 2006/0247262 A1 | 11/2006 | Baenteli et al. |
| 2007/0004626 A1 | 1/2007 | Masuda et al. |
| 2007/0129362 A1 | 6/2007 | Bhamidipati et al. |
| 2007/0197782 A1 | 8/2007 | Clough et al. |

FOREIGN PATENT DOCUMENTS

| | | |
|---|---|---|
| EP | 1392684 B1 | 9/2006 |
| JP | 2004203748 A | 12/2002 |
| WO | WO02096905 A1 | 12/2002 |
| WO | WO03057659 A1 | 7/2003 |

(Continued)

*Primary Examiner* — D M Seaman
(74) *Attorney, Agent, or Firm* — Eric A. Meade; Catherine D. Fitch

(57) ABSTRACT

The invention provides certain 3-pyridyl carboxamide-containing compounds of the Formula (I) (I) or pharmaceutically acceptable salts thereof, wherein A and B are as defined herein. The invention also provides pharmaceutical compositions comprising such compounds, and methods of using the compounds for treating diseases or conditions mediated by Spleen Tyrosine Kinase (Syk) kinase.

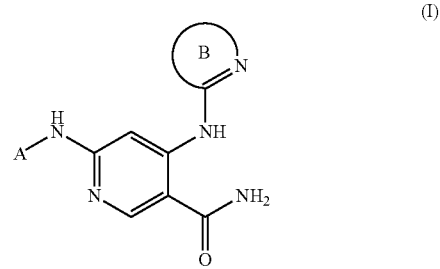

17 Claims, No Drawings

(56) References Cited

FOREIGN PATENT DOCUMENTS

| | | |
|---|---|---|
| WO | WO03078404 A1 | 9/2003 |
| WO | WO2004080463 A1 | 9/2004 |
| WO | WO2004087698 A2 | 10/2004 |
| WO | WO2004087699 A2 | 10/2004 |
| WO | WO2005013996 A2 | 2/2005 |
| WO | WO2005026158 A1 | 3/2005 |
| WO | WO2005028475 A2 | 3/2005 |
| WO | WO2005033103 A1 | 4/2005 |
| WO | WO2005056547 A2 | 6/2005 |
| WO | WO2006004865 A1 | 1/2006 |
| WO | WO2006028833 A1 | 3/2006 |
| WO | WO2006050480 A2 | 5/2006 |
| WO | WO2006068770 A1 | 6/2006 |
| WO | WO2006078846 A1 | 7/2006 |
| WO | WO2006093247 A1 | 9/2006 |
| WO | WO2006129100 A1 | 12/2006 |
| WO | WO2006133426 A2 | 12/2006 |
| WO | WO2006135915 A2 | 12/2006 |
| WO | WO2007009681 A1 | 1/2007 |
| WO | WO2007009773 A1 | 1/2007 |
| WO | WO2007028445 A1 | 3/2007 |
| WO | WO2007042298 A1 | 4/2007 |
| WO | WO2007042299 A1 | 4/2007 |
| WO | WO2007070872 A1 | 6/2007 |
| WO | WO2007085540 A1 | 8/2007 |
| WO | WO2007107469 A2 | 9/2007 |
| WO | WO2007120980 A2 | 10/2007 |
| WO | WO2009031011 A2 | 3/2009 |
| WO | WO2009084695 A1 | 7/2009 |
| WO | WO2009097287 A1 | 8/2009 |
| WO | WO2009102468 A2 | 8/2009 |
| WO | WO2009131687 A2 | 10/2009 |
| WO | WO2009136995 A2 | 11/2009 |
| WO | WO2009145856 A1 | 12/2009 |
| WO | WO2010027500 A1 | 3/2010 |
| WO | WO2010068257 A1 | 6/2010 |
| WO | WO2010068258 A1 | 6/2010 |
| WO | WO2010129802 A1 | 11/2010 |

* cited by examiner

3-PYRIDYL CARBOXAMIDE-CONTAINING SPLEEN TYROSINE KINASE (SYK) INHIBITORS

CROSS REFERENCE TO RELATED APPLICATIONS

This application is a U.S. National Phase application under 35 U.S.C. §371 of PCT Application No. PCT/US2012/058218, filed Oct. 1, 2012, which claims priority under 35 U.S.C. §119(e) from U.S. Provisional Application No. 61/543,545, filed Oct. 5, 2011.

FIELD OF THE INVENTION

The present invention relates to certain 3-pyridyl carboxamide-containing compounds of the Formula (I) (also referred to herein as the "compounds of the Formula (I)" or "compounds of Formula (I)") which are inhibitors of Spleen Tyrosine Kinase (Syk) kinase activity. The present invention also provides compositions comprising such compounds, and methods of using such compounds for treating conditions or disorders associated with inappropriate Syk activity, in particular in the treatment and prevention of disease states mediated by Syk. Such disease states may include inflammatory, allergic and autoimmune diseases, for example, asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, idiopathic thrombocytopenic purpura (ITP), multiple sclerosis, cancer, HIV and lupus.

BACKGROUND OF THE INVENTION

Spleen Tyrosine Kinase (Syk) is a protein tyrosine kinase which has been described as a key mediator of immunoreceptor signalling in a host of inflammatory cells including mast cells, B-cells, macrophages and neutrophils. These immunoreceptors, including Fc receptors and the B-cell receptor, are important for both allergic diseases and antibody-mediated autoimmune diseases and thus pharmacologically interfering with Syk could conceivably treat these disorders.

Allergic rhinitis and asthma are diseases associated with hypersensitivity reactions and inflammatory events involving a multitude of cell types including mast cells, eosinophils, T cells and dendritic cells. Following exposure to allergen, high affinity immunoglobulin receptors for IgE and IgG become cross-linked and activate downstream processes in mast cells and other cell types leading to the release of pro-inflammatory mediators and airway spasmogens. In the mast cell, for example, IgE receptor cross-linking by allergen leads to release of mediators including histamine from pre-formed granules, as well as the synthesis and release of newly synthesized lipid mediators including prostaglandins and leukotrienes.

Syk kinase is a non-receptor linked tyrosine kinase which is important in transducing the downstream cellular signals associated with cross-linking $Fc_{epsilon}RI$ and or $Fc_{epsilon}RI$ receptors, and is positioned early in the signalling cascade. In mast cells, for example, the early sequence of $Fc_{epsilon}RI$ signalling following allergen cross-linking of receptor-IgE complexes involves first Lyn (a Src family tyrosine kinase) and then Syk. Inhibitors of Syk activity would therefore be expected to inhibit all downstream signalling cascades thereby alleviating the immediate allergic response and adverse events initiated by the release of pro-inflammatory mediators and spasmogens (Wong et al. 2004, *Expert Opin. Investig. Drugs* (2004) 13 (7) 743-762).

Recently, it has been shown that the Syk kinase inhibitor R112 (Rigel), dosed intranasally in a phase I/II study for the treatment of allergic rhinitis, gave a statistically significant decrease in PGD2, a key immune mediator that is highly correlated with improvements in allergic rhinorrhea, as well as being safe across a range of indicators, thus providing the first evidence for the clinical safety and efficacy of a topical Syk kinase inhibitor. (Meltzer, Eli O.; Berkowitz, Robert B.; Grossbard, Elliott B, *Journal of Allergy and Clinical Immunology* (2005), 115(4), 791-796). In a more recent phase II clinical trial for allergic rhinitis (Clinical Trials.gov Identifier NCT0015089), R112 was shown as having a lack of efficacy versus placebo.

Rheumatoid Arthritis (RA) is an auto-immune disease affecting approximately 1% of the population. It is characterised by inflammation of articular joints leading to debilitating destruction of bone and cartilage. Recent clinical studies with Rituximab, which causes a reversible B cell depletion, (J. C. W. Edwards et al. 2004, *New Eng. J. Med.* 350: 2572-2581) have shown that targeting B cell function is an appropriate therapeutic strategy in auto-immune diseases such as RA. Clinical benefit correlates with a reduction in auto-reactive antibodies (or Rheumatoid Factor) and these studies suggest that B cell function and indeed auto-antibody production are central to the ongoing pathology in the disease.

Studies using cells from mice deficient in the Spleen Tyrosine Kinase (Syk) have demonstrated a non-redundant role of this kinase in B cell function. The deficiency in Syk is characterised by a block in B cell development (M. Turner et al. 1995 Nature 379: 298-302 and Cheng et al. 1995, *Nature* 378: 303-306). These studies, along with studies on mature B cells deficient in Syk (Kurasaki et al. 2000, *Immunol. Rev.* 176:19-29), demonstrate that Syk is required for the differentiation and activation of B cells. Hence, inhibition of Syk in RA patients is likely to block B cell function, and thereby reduce Rheumatoid Factor production. In addition to the role of Syk in B cell function, and of further relevance to the treatment of RA, is the requirement for Syk activity in Fc receptor (FcR) signalling. FcR activation by immune complexes in RA has been suggested to contribute to the release of multiple pro-inflammatory mediators.

SUMMARY OF THE INVENTION

The present invention provides novel compounds that are potent inhibitors of Syk as well as pharmaceutical compositions containing them. As Syk inhibitors compounds of Formula (I) are useful in the treatment and prevention of diseases and disorders mediated by the Syk protein; such diseases and disorders include, but are not limited to, rheumatoid arthritis, asthma, COPD, cancer and idiopathic thrombocytopenic purpura.

DETAILED DESCRIPTION OF THE INVENTION

Compounds of the Invention

The present invention provides compound of Formula (I) or pharmaceutically acceptable salts thereof, wherein A and B are as defined below. Described below are embodiments of the compound of Formula (I). The compound of Formula (IA), as is described below, is an embodiment of the compound of Formula (I).

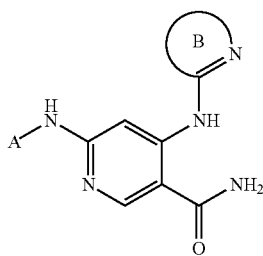
(I)

In embodiment no. 1, the present invention provides a compound of the Formula (I): or a pharmaceutically acceptable salt thereof, wherein B is pyridyl or quinolinyl;
  wherein B is unsubstituted or substituted by 1 to 3 $R^3$ moieties, wherein each $R^3$ moiety is independently selected from the group consisting of $C_1$-$C_3$ alkyl, $C_1$-$C_3$ alkoxy, $C_1$-$C_3$ fluoroalkyl, $C_1$-$C_3$ hydroxyalkyl, halo, hydroxy, amino, ($C_1$-$C_3$ alkyl)amino, di($C_1$-$C_3$ alkyl) amino, and E;
    wherein E is a 5-membered heteroaryl containing 1 to 3 N atoms, wherein E is unsubstituted or substituted by 1 to 2 moieties independently selected from the group consisting of $C_1$-$C_3$ alkyl;

A is selected from the group consisting of:

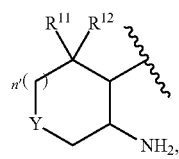
(a)

wherein
  Y is —$CH_2$— or —O—;
  $R^{11}$ and $R^{12}$ are independently H or F; and
  n' is 0 or 1; and

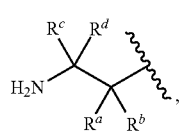
(b)

wherein
  $R^a$ and $R^b$ are independently H or $C_1$-$C_6$ alkyl;
  $R^c$ is H, $C_1$-$C_6$ alkyl, $C_1$-$C_3$ fluoroalkyl, $C_3$-$C_6$ cycloalkyl, or —$(CH_2)_r R^{13}$,
    wherein $R^{13}$ is H or $C_1$-$C_3$ alkyl; and
    r is 1 or 2;
  $R^d$ is H or $C_1$-$C_6$ alkyl,
  or $R^c$ and $R^d$ together with the carbon atom to which they are attached form a group of the formula

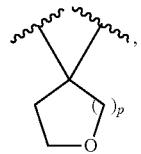

wherein p is 1 or 2.

In embodiment no. 2, B is substituted by no more than 2 $R^3$ moieties, and no more than 1 of said $R^3$ moieties is E, and the remaining variables are as described in embodiment no. 1.

In embodiment no. 3, B is substituted by 1 to 3 $R^3$ moieties, one of said $R^3$ moieties is E, and the remaining variables are as described in embodiment no. 1 and 2.

In embodiment no. 4, A is

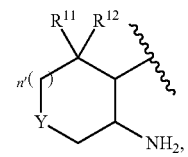

wherein
  Y is —$CH_2$— or —O—;
  $R^{11}$ and $R^{12}$ are independently H or F; and
  n' is 0 or 1; and the remaining variables are as described in any one of embodiment nos. 1-3.

In embodiment no. 5, A is selected from the group consisting of

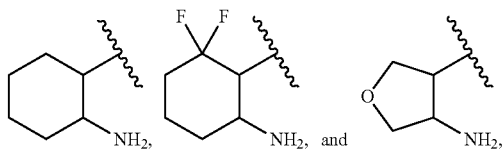

and the remaining variables are as described in any one of embodiment nos. 1-3.

In embodiment no. 6, A is selected from the group consisting of

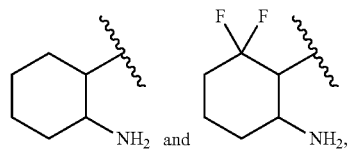

and the remaining variables are as described in any one of embodiment nos. 1-3.

In embodiment no. 7, A is

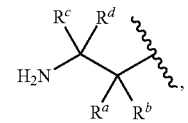

$R^a$ and $R^b$ are independently H or $C_1$-$C_6$ alkyl;

$R^c$ is H, $C_1$-$C_6$ alkyl, $C_1$-$C_3$ fluoroalkyl, $C_3$-$C_6$ cycloalkyl, or —$(CH_2)_rOR^{13}$,
  wherein $R^{13}$ is H or $C_1$-$C_3$ alkyl; and
  r is 1 or 2;

$R^d$ is H or $C_1$-$C_6$ alkyl, or $R^c$ and $R^d$ together with the carbon atom to which they are attached form a group of the formula wherein p is 1 or 2; and the remaining variables are as described in any one of embodiment nos. 1-3.

In embodiment no. 8, the compound of the Formula (I) has the Formula (IA)

(IA)

or a pharmaceutically acceptable salt thereof, wherein $R^{3a}$ is halo, $C_1$-$C_3$ alkyl, $C_1$-$C_3$ fluoroalkyl, or a 5-membered heteroaryl containing 1 to 3 N atoms;
  wherein said heteroaryl of $R^{3a}$ is unsubstituted or substituted by 1 to 2 moieties selected from the group consisting of $C_1$-$C_3$ alkyl;

$R^{ab}$ is H, $C_1$-$C_3$ alkyl, halo, or a 5-membered heteroaryl containing 1 to 3 N ring atoms;
  wherein said heteroaryl of $R^{ab}$ is unsubstituted or substituted by 1 to 2 moieties selected from the group consisting of $C_1$-$C_3$ alkyl;

or $R^{3a}$ and $R^{ab}$ together with the carbon atoms to which they are attached form a phenyl ring;

$R^{3c}$ is H, $C_1$-$C_3$ alkyl, halo, or a 5-membered heteroaryl containing 1 to 3 N atoms;
  wherein said heteroaryl of $R^{3c}$ is unsubstituted or substituted by 1 to 2 moieties selected from the group consisting of $C_1$-$C_3$ alkyl;

A is selected from the group consisting of:

(a)

wherein $R^{11}$ and $R^{12}$ are independently H or F; and (b)

wherein $R^a$ and $R^b$ are independently H or $C_1$-$C_6$ alkyl;

$R^c$ is H, $C_1$-$C_6$ alkyl, $C_1$-$C_3$ fluoroalkyl, $C_3$-$C_6$ cycloalkyl, or —$(CH_2)_rOR^{13}$,
  wherein $R^{13}$ is H or $C_1$-$C_3$ alkyl; and
  r is 1 or 2;

$R^d$ is H or $C_1$-$C_6$ alkyl.

In embodiment no. 9, $R^{3a}$ is $C_1$-$C_3$ alkyl, $C_1$-$C_3$ fluoroalkyl, or a 5-membered heteroaryl containing 1 to 3 N atoms;
  wherein said heteroaryl of $R^{3a}$ is unsubstituted or substituted by 1 to 2 moieties selected from the group consisting of $C_1$-$C_3$ alkyl;

$R^{3b}$ is H, $C_1$-$C_3$ alkyl, halo, or a 5-membered heteroaryl containing 1 to 3 N ring atoms;
  wherein said heteroaryl of $R^{3b}$ is unsubstituted or substituted by 1 to 2 moieties selected from the group consisting of $C_1$-$C_3$ alkyl;

$R^{3c}$ is H, $C_1$-$C_3$ alkyl, halo, or a 5-membered heteroaryl containing 1 to 3 N atoms;
  wherein said heteroaryl of $R^{3c}$ is unsubstituted or substituted by 1 to 2 moieties selected from the group consisting of $C_1$-$C_3$ alkyl, and the remaining variables are as described in embodiment no. 8.

In embodiment no. 10, the moiety and the remaining variables are as described in embodiment no. 8.

In embodiment no. 11, A selected from the group consisting of and the remaining variables are as described in any one of embodiment nos. 8-10.

In embodiment no. 12, A selected from the group consisting of

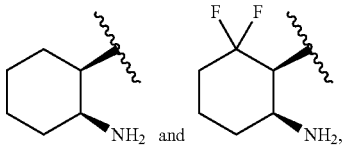

and the remaining variables are as described in any one of embodiment nos. 8-10.

In embodiment no. 13, A is

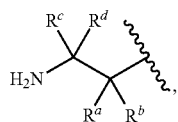

wherein
$R^a$ and $R^b$ are independently H or $C_1$-$C_6$ alkyl;
$R^c$ is H, $C_1$-$C_6$ alkyl, $C_1$-$C_3$ fluoroalkyl, $C_3$-$C_6$ cycloalkyl, or —$(CH_2)_rOR^{13}$,
    wherein $R^{13}$ is H or $C_1$-$C_3$ alkyl; and
    r is 1 or 2;
$R^d$ is H, $C_1$-$C_6$ alkyl,
and the remaining variables are as described in any one of embodiment nos. 8-10.

In embodiment no. 14, A is

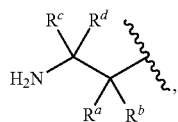

wherein
$R^a$ and $R^b$ are H;
$R^c$ is H or $C_1$-$C_6$ alkyl; and
$R^d$ is H;
and the remaining variables are as described in any one of embodiment nos. 8-10.

Representative compounds of the present invention are as follows, as well as pharmaceutically acceptable salts thereof:
rel-6-{[(1R,2S)-2-aminocyclohexyl]amino}-4-[(6-methylpyridin-2-yl)amino]pyridine-3-carboxamide;
6-[(2-aminoethyl)amino]-4-[(6-methylpyridin-2-yl)amino]pyridine-3-carboxamide;
rel-6-{[(1R,2S)-2-aminocyclohexyl]amino}-4-{[6-(2H-1,2,3-triazol-2-yl)pyridin-2-yl]amino}pyridine-3-carboxamide;
rel-6-{[(1R,2S)-2-aminocyclohexyl]amino}-4-[(4,6-dimethylpyridin-2-yl)amino]pyridine-3-carboxamide;
rel-6-{[(1R,2S)-2-aminocyclohexyl]amino}-4-(quinolin-2-ylamino)pyridine-3-carboxamide;
rel-6-{[(1R,2S)-2-aminocyclohexyl]amino}-4-[(5-fluoro-6-methylpyridin-2-yl)amino]pyridine-3-carboxamide;
6-{[2-aminopropyl]amino}-4-{[4,6-bis(1-methyl-1H-pyrazol-4-yl)pyridin-2-yl]amino}pyridine-3-carboxamide;
6-{[2-aminopropyl]amino}-4-{[6-methyl-5-(1-methyl-1-pyrazol-4-yl)pyridin-2-yl]amino}pyridine-3-carboxamide;
rel-6-{[(1R,2S)-2-aminocyclohexyl]amino}-4-{[6-(trifluoromethyl)pyridin-2-yl]amino}pyridine-3-carboxamide;
6-[(2-aminoethyl)amino]-4-[(4,6-dimethylpyridin-2-yl)amino]pyridine-3-carboxamide;
6-[(2-amino-3,3,3-trifluoropropyl)amino]-4-[(4,6-dimethylpyridin-2-yl)amino]pyridine-3-carboxamide;
rel-6-{[(3S,4S)-4-aminotetrahydrofuran-3-yl]amino}-4-[(4,6-dimethylpyridin-2-yl)amino]pyridine-3-carboxamide;
6-{[(4-aminotetrahydro-2H-pyran-4-yl)methyl]amino}-4-[(4,6-dimethylpyridin-2-yl)amino]pyridine-3-carboxamide;
6-{[(3-aminotetrahydrofuran-3-yl)methyl]amino}-4-[(4,6-dimethylpyridin-2-yl)amino]pyridine-3-carboxamide;
6-{[2-amino-3-methoxypropyl]amino}-4-[(6-methylpyridin-2-yl)amino]pyridine-3-carboxamide;
rel-6-{[(1R,2R)-2-aminocyclohexyl]amino}-4-[(6-methylpyridin-2-yl)amino]pyridine-3-carboxamide;
6-[(2-amino-2-methylbutyl)amino]-4-[(6-methylpyridin-2-yl)amino]pyridine-3-carboxamide;
6-[(2-aminobutyl)amino]-4-[(6-methylpyridin-2-yl)amino]pyridine-3-carboxamide;
6-[(2-amino-1-methylethyl)amino]-4-[(4,6-dimethylpyridin-2-yl)amino]pyridine-3-carboxamide;
6-[(2-aminopentyl)amino]-4-[(6-methylpyridin-2-yl)amino]pyridine-3-carboxamide;
6-[(2-amino-2-cyclopropylethyl)amino]-4-[(6-methylpyridin-2-yl)amino]pyridine-3-carboxamide;
6-[(2-aminoethyl)amino]-4-[(5-bromo-6-methylpyridin-2-yl)amino]pyridine-3-carboxamide;
6-{[2-aminopropyl]amino}-4-[(4,6-dimethylpyridin-2-yl)amino]pyridine-3-carboxamide; and
rel-6-{[(1S,6S)-6-amino-2,2-difluorocyclohexyl]amino}-4-[(4,6-dimethylpyridin-2-yl)amino]pyridine-3-carboxamide.

Further representative compounds of the present invention are as follows, as well as pharmaceutically acceptable salts thereof:
6-{[(1R,2S)-2-aminocyclohexyl]amino}-4-[(6-methylpyridin-2-yl)amino]pyridine-3-carboxamide;
6-[(2-aminoethyl)amino]-4-[(6-methylpyridin-2-yl)amino]pyridine-3-carboxamide;
6-{[(1R,2S)-2-aminocyclohexyl]amino}-4-{[6-(2H-1,2,3-triazol-2-yl)pyridin-2-yl]amino}pyridine-3-carboxamide;
6-{[(1R,2S)-2-aminocyclohexyl]amino}-4-[(4,6-dimethylpyridin-2-yl)amino]pyridine-3-carboxamide;
6-{[(1R,2S)-2-aminocyclohexyl]amino}-4-(quinolin-2-ylamino)pyridine-3-carboxamide;
6-{[(1R,2S)-2-aminocyclohexyl]amino}-4-[(5-fluoro-6-methylpyridin-2-yl)amino]pyridine-3-carboxamide;
6-{[(2S)-2-aminopropyl]amino}-4-{[4,6-bis(1-methyl-1H-pyrazol-4-yl)pyridin-2-yl]amino}pyridine-3-carboxamide;
6-{[(2S)-2-aminopropyl]amino}-4-{[6-methyl-5-(1-methyl-1-pyrazol-4-yl)pyridin-2-yl]amino}pyridine-3-carboxamide;
6-{[(1R,2S)-2-aminocyclohexyl]amino}-4-{[6-(trifluoromethyl)pyridin-2-yl]amino}pyridine-3-carboxamide;
6-[(2-aminoethyl)amino]-4-[(4,6-dimethylpyridin-2-yl)amino]pyridine-3-carboxamide;
6-[(2-amino-3,3,3-trifluoropropyl)amino]-4-[(4,6-dimethylpyridin-2-yl)amino]pyridine-3-carboxamide;
rel-6-{[(3S,4S)-4-aminotetrahydrofuran-3-yl]amino}-4-[(4,6-dimethylpyridin-2-yl)amino]pyridine-3-carboxamide;
6-{[(4-aminotetrahydro-2H-pyran-4-yl)methyl]amino}-4-[(4,6-dimethylpyridin-2-yl)amino]pyridine-3-carboxamide;

6-{[(3-aminotetrahydrofuran-3-yl)methyl]amino}-4-[(4,6-dimethylpyridin-2-yl)amino]pyridine-3-carboxamide;
6-{[(2R)-2-amino-3-methoxypropyl]amino}-4-[(6-methylpyridin-2-yl)amino]pyridine-3-carboxamide;
rel-6-{[(1R,2R)-2-aminocyclohexyl]amino}-4-[(6-methylpyridin-2-yl)amino]pyridine-3-carboxamide;
6-[(2-amino-2-methylbutyl)amino]-4-[(6-methylpyridin-2-yl)amino]pyridine-3-carboxamide;
6-[(2-aminobutyl)amino]-4-[(6-methylpyridin-2-yl)amino]pyridine-3-carboxamide;
6-[(2-amino-1-methylethyl)amino]-4-[(4,6-dimethylpyridin-2-yl)amino]pyridine-3-carboxamide;
6-[(2-aminopentyl)amino]-4-[(6-methylpyridin-2-yl)amino]pyridine-3-carboxamide;
6-[(2-amino-2-cyclopropylethyl)amino]-4-[(6-methylpyridin-2-yl)amino]pyridine-3-carboxamide;
6-[(2-aminoethyl)amino]-4-[(5-bromo-6-methylpyridin-2-yl)amino]pyridine-3-carboxamide;
6-{[(2S)-2-aminopropyl]amino}-4-[(4,6-dimethylpyridin-2-yl)amino]pyridine-3-carboxamide;
6-{[(1R,6R)-6-amino-2,2-difluorocyclohexyl]amino}-4-[(4,6-dimethylpyridin-2-yl)amino]pyridine-3-carboxamide; and
6-{[(1S,6S)-6-amino-2,2-difluorocyclohexyl]amino}-4-[(4,6-dimethylpyridin-2-yl)amino]pyridine-3-carboxamide.

The invention also provides a compound of Formula (I) or a pharmaceutically acceptable salt thereof in purified form.

DEFINITIONS

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "–O-alkyl," etc.

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "therapeutically effective amount" as used herein, refers to an amount of the compound of Formula (I) and/or an additional therapeutic agent, or a composition thereof that is effective in producing the desired therapeutic, ameliorative, inhibitory or preventative effect when administered to a patient suffering from a disease or condition mediated by Syk. In the combination therapies of the present invention, a therapeutically effective amount can refer to each individual agent or to the combination as a whole, wherein the amounts of all agents administered are together effective, but wherein the component agent of the combination may not be present individually in an effective amount.

The term "preventing," as used herein with respect to a disease or condition mediated by Syk, refers to reducing the likelihood of the disease or condition.

The term "alkyl," as used herein, refers to an aliphatic hydrocarbon group having one of its hydrogen atoms replaced with a bond having the specified number of carbon atoms. In different embodiments, an alkyl group contains from 1 to 6 carbon atoms ($C_1$-$C_6$ alkyl) or from 1 to 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

The term "alkoxy" as used herein, refers to an —O-alkyl group, wherein an alkyl group is as defined above. Non-limiting examples of alkoxy groups include methoxy, ethoxy, n-propoxy, isopropoxy, n-butoxy and t-butoxy. An alkoxy group is bonded via its oxygen atom.

The term "aryl," as used herein, refers to an aromatic monocyclic or multicyclic ring system comprising from about 6 to about 14 carbon atoms. In one embodiment, an aryl group contains from about 6 to 10 carbon atoms ($C_6$-$C_{10}$ aryl). In another embodiment an aryl group is phenyl. Non-limiting examples of aryl groups include phenyl and naphthyl.

The term "cycloalkyl," as used herein, refers to a saturated ring containing the specified number of ring carbon atoms, and no heteroatom. In a like manner the term "$C_3$-$C_6$ cycloalkyl" refers to a saturated ring having from 3 to 6 ring carbon atoms. Non-limiting examples of monocyclic cycloalkyls include cyclopropyl, cyclobutyl, cyclopentyl, and cyclohexyl.

The term "halo," as used herein, means —F, —Cl, —Br or —I. In one embodiment, a halo group is —F or —Cl. In another embodiment, a halo group is —F.

The term "fluoroalkyl," as used herein, refers to an alkyl group as defined above, wherein one or more of the alkyl group's hydrogen atoms has been replaced with a fluorine atom. In one embodiment, a fluoroalkyl group has from 1 to 6 carbon atoms. In another embodiment, a fluoroalkyl group has from 1 to 3 carbon atoms. In another embodiment, a fluoroalkyl group is substituted with from 1 to 3 fluorine atoms. Non-limiting examples of fluoroalkyl groups include —$CH_2F$, —$CHF_2$, and —$CF_3$. The term "$C_1$-$C_3$ fluoroalkyl" refers to a fluoroalkyl group having from 1 to 3 carbon atoms.

The term "heteroaryl," as used herein, refers to an aromatic monocyclic or multicyclic ring system comprising about 5 to about 14 ring atoms, wherein from 1 to 3 of the ring atoms is independently N, O, or S and the remaining ring atoms are carbon atoms. In one embodiment, a heteroaryl group has 5 to 10 ring atoms. In another embodiment, a heteroaryl group is monocyclic ring system and has 5 or 6 ring atoms. In another embodiment, a heteroaryl group is a bicyclic ring system. A heteroaryl group is joined via a ring carbon atom. The term "heteroaryl" also includes a heteroaryl as defined above fused to a heterocyclyl as defined below. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furyl, pyrrolyl, triazolyl, 1,2,4-thiadiazolyl, pyrazinyl, pyridazinyl, indolyl, quinoxalinyl, phthalazinyl, oxindolyl, imidazo[1,2-a]pyridinyl, imidazo[2,1-b]thiazolyl, and the like. In one embodiment, a heteroaryl group is a 5-membered heteroaryl. In another embodiment, a heteroaryl group is a 6-membered heteroaryl.

The term "heterocyclyl," as used herein, refers to a non-aromatic saturated monocyclic or multicyclic ring system containing 3 to 11 ring atoms, wherein from 1 to 4 of the ring atoms are independently O, S, or N, and the remainder of the ring atoms are carbon atoms. A heterocyclyl group can be joined via a ring carbon or ring nitrogen atom. In one embodiment, a heterocyclyl group is monocyclic and has from 3 to 7 ring atoms. In another embodiment, a heterocyclyl group is monocyclic has from about 4 to 7 ring atoms. In another embodiment, a heterocyclyl group is bicyclic and has from 7 to 11 ring atoms. In still another embodiment, a heterocyclyl group is monocyclic and has 5 or 6 ring atoms. In one embodiment, a heterocyclyl group is monocyclic. In another embodiment, a heterocyclyl group is bicyclic. The nitrogen or sulfur atom of the heterocyclyl can be optionally oxidized to the corresponding N-oxide, S-oxide or S,S-dioxide. Non-limiting examples of monocyclic heterocyclyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, and the like.

In one embodiment, a heterocyclyl group is a 5- to 6-membered monocyclic heterocyclyl. In another embodiment, a heterocyclyl group is a 5-membered monocyclic heterocyclyl. In another embodiment, a heterocyclyl group is a 6-membered monocyclic heterocyclyl. The term "5- to 6-membered heterocyclyl" refers to a monocyclic heterocyclyl group having from 5 to 6 ring atoms.

The term "substituted" means that one or more hydrogens on the atoms of the designated moiety are replaced with a selection from the indicated group, provided that the atoms' normal valencies under the existing circumstances are not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

When any substituent or variable occurs more than one time in any constituent or the compound of Formula (I), its definition on each occurrence is independent of its definition at every other occurrence, unless otherwise indicated.

The term "in purified form," as used herein, refers to the physical state of a compound after the compound is isolated from a synthetic process (e.g., from a reaction mixture), a natural source, or a combination thereof. The term "in purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvates" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula (I) may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

In addition, the prefix "rel", when used in naming a compound that contains two asymmetric carbon atoms, indicates that the relative stereochemistry between the two asymmetric carbon atoms is as described, but that the absolute stereochemistry is unknown. Thus, by way of example, a compound containing two contiguous asymmetric carbon atoms whose chemical name is preceded by the prefix "rel" and which also indicates a "3R,4S" configuration, means that the relationship between the two asymmetric carbon atoms could have the absolute configuration of "(3R,4S)" or the absolute configuration of 3S,4R.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention.

All stereoisomers (for example, geometric isomers, optical isomers and the like) of the present compounds (including those of the salts and solvates of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations.

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66 (1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The present invention further includes the compounds of Formula (I) in all their isolated forms. For example, the above-identified compounds are intended to encompass all forms of the compounds such as, any solvates, hydrates, stereoisomers, and tautomers thereof.

As used herein, the term "composition" is intended to encompass a product comprising the specified ingredients in the specified amounts, as well as any product which results, directly or indirectly, from combination of the specified ingredients in the specified amounts.

In the compounds of generic Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula (I) can be prepared without undue experimentation by conventional techniques well known to those skilled in the art or by processes analogous to those described in the Schemes and Examples herein using appropriate isotopically-enriched reagents and/or intermediates.

Uses of the Compounds

Compounds of Formula (I) or its pharmaceutically acceptable salts and pharmaceutical compositions containing such compounds can be used to treat or prevent a variety of conditions or diseases mediated by Spleen tyrosine kinase (Syk). Such conditions and diseases include, but are not limited to: (1) arthritis, including rheumatoid arthritis, juvenile arthritis, psoriatic arthritis and osteoarthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia including idiopathic thrombopenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenic purpura, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g., precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors) myelomas including multiple myeloma, myeloproliferative disorders kidney cancer, lung cancer, muscle cancer, bone cancer, bladder cancer, brain cancer, melanoma including oral and metastatic melanoma, Kaposi's sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; (14) low grade scarring including scleroderma, increased fibrosis, keloids, post-surgical scars, pulmonary fibrosis, vascular spasms, migraine, reperfusion injury, and post-myocardial infarction.

The invention thus provides compounds of Formula (I) and pharmaceutically acceptable salts thereof for use in therapy, and particularly in the treatment of diseases and conditions mediated by inappropriate Syk activity. The inappropriate Syk activity referred to herein is any Syk activity that deviates from the normal Syk activity expected in a particular patient. Inappropriate Syk activity may take the form of, for instance, an abnormal increase in activity, or an aberration in the timing and or control of Syk activity. Such inappropriate activity may result then, for example, from overexpression or mutation of the protein kinase leading to inappropriate or uncontrolled activation.

In a further embodiment, the present invention is directed to methods of regulating, modulating, or inhibiting Syk for the prevention and/or treatment of disorders related to unregulated Syk activity.

In a further embodiment, the present invention provides a method of treatment of a patient suffering from a disorder mediated by Syk activity, which comprises administering to said patient an effective amount of a compound of Formula (I) or a pharmaceutically acceptable salt, solvate, or a physiologically functional derivative thereof. In a further embodiment, the present invention provides for the use of a compound of Formula (I), or a pharmaceutically acceptable salt or solvate thereof, or a physiologically functional derivative thereof, in the preparation of a medicament for the treatment of a disorder mediated by Syk activity.

In a further embodiment said disorder is rheumatoid arthritis. In yet another embodiment, said disorder is cancer. In a further embodiment said disorder mediated by Syk activity is asthma. In a further embodiment said disorder is ocular conjunctivitis.

Yet another aspect of the present invention provides a method for treating diseases caused by or associated with Fc receptor signaling cascades, including FceRI and/or FcgRI-mediated degranulation as a therapeutic approach towards the treatment or prevention of diseases characterized by, caused by and/or associated with the release or synthesis of chemical mediators of such Fc receptor signaling cascades or degranulation. In addition, Syk is known to play a critical role in immunotyrosine-based activation motif (ITAM) signaling, B cell receptor signaling, T cell receptor signalingand is an essential component of integrin beta (1), beta (2), and beta (3) signaling in neutrophils. Thus, compounds of the present invention can be used to regulate Fc receptor, ITAM, B cell receptor and integrin signalingcascades, as well as the cellular responses elicited through these signaling cascades. Non-limiting examples of cellular responses that may be regulated or inhibited include respiratory burst, cellular adhesion, cellular degranulation, cell spreading, cell migration, phagocytosis, calcium ion flux, platelet aggregation and cell maturation.

Compositions and Administration

While it is possible that, for use in therapy, a compound of Formula (I), as well as pharmaceutically acceptable salts thereof, may be administered as the raw chemical, it is possible to present the active ingredient as a pharmaceutical composition. Accordingly, the invention further provides a pharmaceutical composition, which comprises a compound of Formula (I) and pharmaceutically acceptable salts thereof, and a pharmaceutically acceptable carrier. The compounds of the Formula (I) and pharmaceutically acceptable salts thereof, are as described above. The carriers must be acceptable in the sense of being compatible with the other ingredients of the formulation and not deleterious to the recipient thereof. In accordance with another aspect of the invention there is also provided a process for the preparation of a pharmaceutical composition including admixing a compound of the Formula (I), or a pharmaceutically acceptable salt thereof, with one or more pharmaceutically acceptable carriers.

Pharmaceutical compositions of the present invention may be presented in unit dose forms containing a predetermined amount of active ingredient per unit dose. Such a unit may contain, for example, 5 µg to 1 g, preferably 1 mg to 700 mg, more preferably 5 mg to 100 mg of a compound of the Formula (I), depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, or parenteral (including intravenous and intramuscular) route. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, COPD or ARDS.

In a further embodiment, the present invention provides a pharmaceutical composition adapted for administration by the inhaled route, for treating, for example, asthma or COPD.

In a further embodiment, the present invention provides a pharmaceutical composition adapted for administration by the ocular route, for treating, diseases of the eye, for example, conjunctivitis.

In a further embodiment, the present invention provides a pharmaceutical composition adapted for administration by the parenteral (including intravenous) route, for treating, for example, cancer.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release, for example, by coating or embedding particulate material in polymers, wax or the like.

The compounds of Formula (I) and pharmaceutically acceptable salts thereof can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Dosage forms for inhaled administration may conveniently be formulated as aerosols or dry powders.

For compositions suitable and/or adapted for inhaled administration, it is preferred that the compound or salt of Formula (I) is in a particle-size-reduced form, and more preferably the size-reduced form is obtained or obtainable by micronisation. The preferable particle size of the size-reduced (e.g., micronised) compound or salt or solvate is defined by a D50 value of about 0.5 to about 10 microns (for example as measured using laser diffraction).

Aerosol formulations, e.g., for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g., co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of Formula (I) or salt or solvate thereof (preferably in particle-size-reduced form, e.g., in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of Formula (I) or salt thereof. The lactose is preferably lactose hydrate e.g., lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g., 10-1000 microns e.g., 30-1000 microns) in diameter, and/or 50% or more of the lactose particles being less than 500 microns (e.g., 10-500 microns) in diameter. More preferably, the particle size of the lactose is defined by 90% or more of the lactose particles being less than 300 microns (e.g., 10-300 microns e.g., 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g., about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g., containing the dry powder composition) mounted longitudinally in a strip or ribbon inside a suitable inhalation device. The container is rupturable or peel-openable on demand and the dose of e.g., the dry powder composition can be administered by inhalation via the device such as the DISKUS® device (GlaxoSmithKline). Other dry powder inhalers are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler (Merck), Turbuhaler® (AstraZeneca), Ultrahaler® (Aventis), and the like.

Dosage forms for ocular administration may be formulated as solutions or suspensions with excipients suitable for ophthalmic use.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurised aerosols, nebulizers or insufflators.

For pharmaceutical compositions suitable and/or adapted for intranasal administration, the compound of Formula (I) or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

The following are examples of representative pharmaceutical dosage forms for the compounds of this invention:

| Injectable Suspension (I.M.) | mg/mL |
|---|---|
| Compound of Formula (I) | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula (I) | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula (I) | 25 |
| Lactose Powder | 573.5 |
| Magnesium Stearate | 1.5 |
| | 600 |

| Aerosol | Per canister |
|---|---|
| Compound of Formula (I) | 24 mg |
| Lecithin, NF Liquid Concentrate | 1.2 mg |
| Trichlorofluoromethane, NF | 4.025 gm |
| Dichlorodifluoromethane, NF | 12.15 gm |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of Formula (I) for the treatment of diseases or conditions associated with inappropriate Syk activity, will generally be in the range of 5 µg to 100 mg/kg body weight of recipient (patient) per day and more usually in the range of 5 µg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of Formula (I) per se.

The compositions of the invention can further comprise one or more additional therapeutic agents, as discussed in further detail below. Accordingly, in one embodiment, the present invention provides compositions comprising: (i) a compound of Formula (I) or a pharmaceutically acceptable salt thereof; (ii) one or more additional therapeutic agents, that are not compounds of Formula (I); and (iii) a pharmaceutically acceptable carrier, wherein the amounts in the composition are together effective to treat one of the disease or conditions discussed above.

Combination Therapy

The compounds of Formula (I) or their pharmaceutically acceptable salts may be used in combination, either in a single formulation or co-administered as separate formulations with at least one additional therapeutic agent to treat or prevent the diseases and conditions described herein. These additional therapeutic agents include, but are not limited to: (1) a DP receptor antagonist, such as S-5751 and laropiprant; (2) a corticosteroid, such as triamcinolone acetonide, budesonide, beclomethasone, fluticasone and mometasone; (3) a β2-adrenergic agonist, such as salmeterol, formoterol, arformoterol, terbutaline, metaproterenol, albuterol and the like; (4) a leukotriene modifier, including a leukotriene receptor antagonist, such as montelukast, zafirlukast, pranlukast, or a lipooxygenase inhibitor including 5-lipooxygenase inhibitors and FLAP (5-lipooxygenase activating protein) inhibitors, such as zileuton; (5) an antihistamine such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (6) a decongestant, including phenylephrine, phenylpropanolamine, pseudophedrine, oxymetazoline, ephinephrine, naphazoline, xylometazoline, propylhexedrine, or levo-desoxyephedrine; (7) an antiitussive, including codeine, hydrocodone, caramiphen, carbetapentane, or dextramethorphan; (8) another prostaglandin ligand, including prostaglandin F agonist such as latanoprost; misoprostol, enprostil, rioprostil, ornoprostol or rosaprostol; (9) a diuretic; (10) non-steroidal antiinflammatory agents (NSAIDs), such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (11) cyclooxygenase-2 (COX-2) inhibitors, such as celecoxib and rofecoxib; (12) inhibitors of phosphodiesterase type IV (PDE-IV) e.g., Ariflo, roflumilast; (13) antagonists of the chemokine receptors, especially CCR-1, CCR-2, and CCR-3; (14) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (15) anti-diabetic agents such as insulin, sulfonylureas, biguanides (metformin), α-glucosidase inhibitors (acarbose) and glitazones (troglitazone, pioglitazone, englitazone, rosiglitazone and the like); (16) preparations of interferon beta (interferon beta-1a, interferon beta-1b); (17) anticholinergic agents, such as muscarinic antagonists (ipratropium bromide and tiotropium bromide), as well as selective muscarinic M3 antagonists; (18) steroids such as beclomethasone, methylprednisolone, betamethasone, prednisone, dexamethasone, and hydrocortisone; (19) triptans commonly used for the treatment of migraine such as sumitriptan and rizatriptan; (20) alendronate and other treatments for osteoporosis; (21) other compounds such as 5-aminosalicylic acid and prodrugs thereof, antimetabolites such as azathioprine and 6-mercaptopurine, cytotoxic cancer chemotherapeutic agents, bradykinin (BK2) antagonists such as FK-3657, TP receptor antagonists such as seratrodast, neurokinin antagonists (NK1/NK2), VLA-4 antagonists, such as those described in U.S. Pat. No. 5,510,332, WO97/03094, WO97/02289, WO96/40781, WO96/22966, WO96/20216, WO96/01644, WO96/06108, WO95/15973 and WO96/31206. In addition, the invention encompasses a method of treating prostaglandin D2 mediated diseases comprising: administration to a patient in need of such treatment a non-toxic therapeutically effective amount of a compound of Formula (I), optionally co-administered with one or more of such ingredients as listed immediately above.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like.

In one embodiment, the compound of Formula (I) is administered during a time when the additional therapeutic agent(s) exert their prophylactic or therapeutic effect, or vice versa.

In another embodiment, the compound of Formula (I) and the additional therapeutic agent(s) are administered in doses commonly employed when such agents are used as monotherapy for treating the disorder.

In another embodiment, the compound of Formula (I) and the additional therapeutic agent(s) are administered in doses lower than the doses commonly employed when such agents are used as monotherapy for treating the disorder.

In one embodiment, the compound of Formula (I) and the additional therapeutic agent(s) are present in the same composition, which is suitable for oral administration.

The compound of Formula (I) and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

The doses and dosage regimen of the additional therapeutic agent(s) used in the combination therapies of the present invention for the treatment or prevention of a disease or disorder can be determined by the attending clinician, taking into consideration the approved doses and dosage regimen in the package insert; the age, sex and general health of the patient; and the type and severity of the viral infection or related disease or disorder.

Another aspect of this invention is a kit comprising a therapeutically effective amount of the compound of Formula (I) or a pharmaceutically acceptable salt of said compound, optionally at least one additional therapeutic agent listed above and a pharmaceutically acceptable carrier, vehicle or diluent.

Methods of Preparing the Compounds of Formula (I)

The compounds of this invention may be made by a variety of methods, including standard chemistry. Any previously defined variable will continue to have the previously defined meaning unless otherwise indicated. Illustrative general synthetic methods are set out below and then specific compounds of the Formula (I) are prepared in the Examples.

Compounds of general Formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of protecting groups as well as the reaction conditions and order of reaction steps shall be consistent with the preparation of compounds of Formula (I). Those skilled in the art will recognize whether a stereocenter exists in compounds of Formula (I). Accordingly, the present invention includes all possible stereoisomers and includes not only mixtures of stereoisomers (such as racemic compounds) but the individual stereoisomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994).

The following solvents, reagents, protecting groups, moieties, and other designations may be referred to by their abbreviations in parenthesis:

Me=methyl; Et=ethyl; Pr=propyl; iPr=isopropyl, Bu=butyl; t-Bu=tert-butyl; Ph=phenyl, and Ac=acetyl
µl=microliters
AcOH or HOAc=acetic acid
ACN=acetonitrile
Ad=adamantyl
aq=aqueous
Bn=benzyl
Boc or BOC=tert-butoxycarbonyl
Bz=benzoyl
Cbz=benyzloxycarbonyl
Dba=dibenzylideneacetone
DBU=1,8-Diaza-7-bicyclo[5.4.0]undecene
DCM=dichloromethane
DMAP=4-Dimethylaminopyridine
DIBAL=diisobutylaluminum hydride
DIEA or Hünig's Base=N,N-diisopropylethylamine
DMA=1,2-dimethylacetamide
DMF=dimethylformamide
DMSO=dimethyl sulfoxide
Dppf=1,1'-Bis(diphenylphosphino)ferrocene
DMT=Dimercaptotriazine
DTT=dithiothreitol
EDTA=ethylenediamine tetraacetic acid ESI=Electrospray ionization
EtOAc=ethyl acetate
g=grams
GST=glutathione S-transferase
h=hour
HMDS=1,1,1,3,3,3-hexamethyldisilazane
HATU=N,N,N',N'-tetramethyl-O-(7-azabenzotriazol-1-yl)uronium hexafluorophosphate
HPLC=high-performance liquid chromatography
HOBt=1-hydroxybenzotriazole
LDA=lithium diisopropylamide
LC=liquid chromatography
LCMS=liquid chromatography mass spectrometry
min=minute
mg=milligrams
mL=milliliters
mmol=millimoles
Me=methyl
MeOH=methanol
MS=mass spectrometry
NBS=N-bromosuccimide
NMP=N-methylpyrrolidone
NMR=nuclear magnetic resonance spectroscopy
rac=racemic mixture
RT or rt=room temperature (ambient, about 25° C.)
sat=saturated
SFC=supercritical fluid chromatography
TBSCl=t-butyldimethylsilyl chloride
TBS=t-butyldimethylsilyl
TEA=triethylamine ($Et_3N$)
TFA=trifluoroacetic acid
TFAA=trifluoroacetic anhydride
THF=tetrahydrofuran
TLC=thin layer chromatography
TMS=trimethylsilyl
Tris=tris(hydroxymethyl)aminomethane
Xantphos=4,5-Bis(diphenylphosphino)-9,9-dimethylxanthene General Methods Compounds of the Formula (I) can be prepared according to one of the synthetic schemes procedures set forth in Scheme 1 below, and/or by methods similar to those described in the Examples below.

SCHEME 1

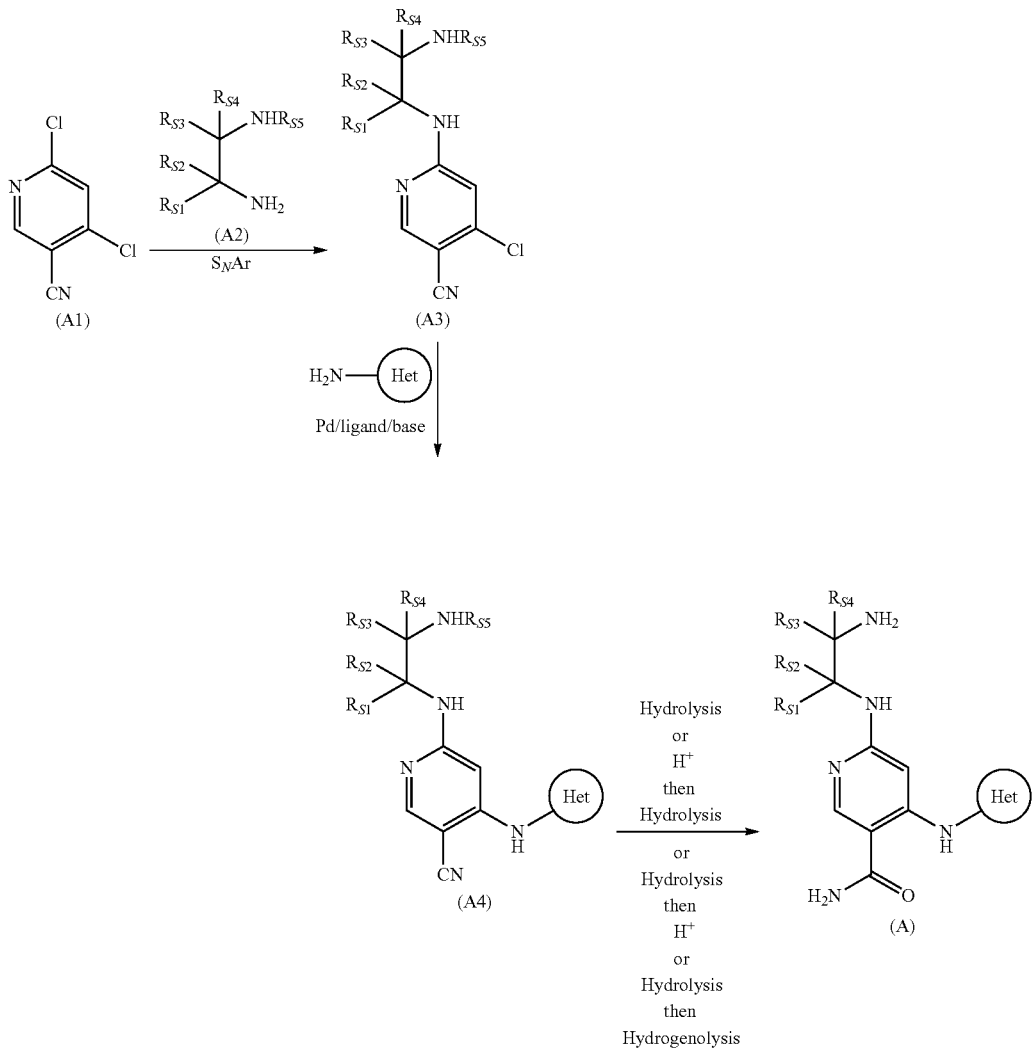

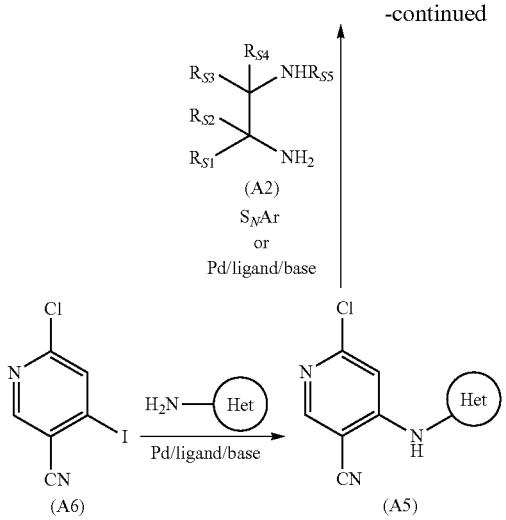

-continued

As shown in Scheme 1, some compounds of structural type A (wherein $R_{S1}$-$R_{S4}$ are various substituents on the ethylenediamine moiety and Het represent various heteroaryl moieties) are prepared from substituted pyridine-3-carbonitriles (A4) (wherein $R_{s5}$ is an alkylamino protecting group) by one of the following methods: a) hydrolysis of the nitrile, or b) acidic deprotection of the alkylamino protecting group followed by hydrolysis of the nitrile, or c) hydrolysis of the nitrile followed by acidic deprotection of the alkylamino protecting group, or d) hydrolysis of the nitrile followed by hydrogenolysis of the alkylamino protecting group. The substituted pyridine-3-carbonitriles (A4) are prepared by the palladium-mediated coupling of an arylamine with substituted 4-chloropyridine-3-carbonitriles (A3), which in turn are prepared by the reaction of 4,6-dichloropyridine-3-carbonitrile (A1) with substituted diamines (A2) via an $S_NAr$ reaction. Alternatively, substituted pyridine-3-carbonitriles (A4) are prepared by the reaction of 6-chloropyridine-3-carbonitriles (5) with substituted diamines (2) either with $S_NAr$ or palladium-mediated conditions. The 6-chloropyridine-3-carbonitriles (5) are prepared by the palladium-mediated coupling of arylamines with 6-chloro-4-iodopyridine-3-carbonitrile (6).

Compounds of Formulas (I) are prepared according to the procedures described in Scheme I above and in the Examples below, using appropriate materials, and are further exemplified by the following specific examples. The compounds exemplified are illustrative of the invention and are not, however, to be construed as limiting the scope of the invention in any manner. The examples further illustrate details for the preparation of the compounds of the present invention. Those skilled in the art will readily understand that known variations of protecting groups, of reagents, as well as of the conditions and processes of the following preparative procedures, can be used to prepare these compounds. It is also understood that whenever a chemical reagent is not commercially available, such a chemical reagent can be readily prepared by those skilled in the art by either following or adapting known methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (ESI).

For ease of reference, various moieties are referred in the Examples below as "A" moieties, "B" moieties, "E" moieties and the "pyridylcarboxamide" moiety. These moieties are illustrated in the structural formula below.

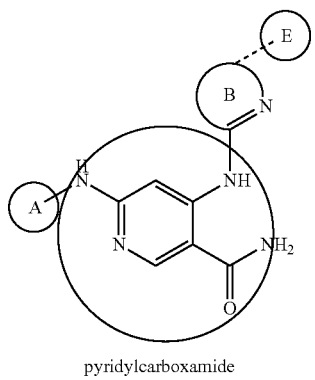

pyridylcarboxamide

The starting materials and reagents used in preparing compounds described are either available from commercial suppliers or were prepared by literature methods known to those skilled in the art.

These examples are being provided to further illustrate the present invention. They are for illustrative purposes only; the scope of the invention is not to be considered limited in any way thereby.

Where mass spectral (MS) data are presented in the examples below, analysis was performed using an Agilent Technologies 6120 quadrupole LC/MS. Resolution of enantiomers was typically performed using supercritical fluid chromatography utilizing a Chiral Technologies AD, AD-H,

EXAMPLES

Preparative Example 1

Preparation of Pyridylcarboxamide Precursors

Preparative Example 1.1 tert-butyl {(1S,2R)-2-[(4-chloro-5-cyanopyridin-2-yl)amino]cyclohexyl}carbamate

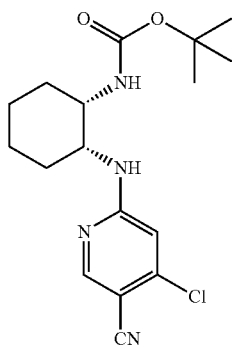 [SMILES: CC(C)(C)OC(=O)N[C@H]1CCCC[C@H]1Nc1cc(Cl)c(C#N)cn1]

Prep Ex. 1.1

4,6-Dichloropyridine-3-carbonitrile (4.35 g, 25.1 mmol), tert-butyl [(1S,2R)-2-aminocyclohexyl]carbamate (commerically available from Small Molecules, Inc.; CAS: 365996-30-1) (5.93 g, 27.7 mmol) and DIEA (6.59 mL, 37.7 mmol) were added to a 20 mL microwave vial. The vial was sealed and heated in a microwave to 150° C. After 15 minutes, the reaction mixture was cooled, the solvent was decanted, and the gelled solids diluted with chloroform (10 mL). The organics were washed with citric acid (1.0 M in water, 15 mL, 15 mmol), dried over sodium sulfate, filtered, and concentrated under reduced pressure. The residue was purified by silica gel chromatography (0-30% acetone/hexanes, linear gradient) to afford two separated regioisomeric products (~1:1). The slower eluting isomer (on silica) was determined to be tert-butyl {(1S,2R)-2-[(4-chloro-5-cyanopyridin-2-yl)amino]cyclohexyl}carbamate. MS ESI calc'd. for $C_{17}H_{24}ClN_4O_2$ $[M+H]^+$ 351. found 351. $^1$H NMR (600 MHz, CDCl$_3$) δ 8.26 (s, 1H), 6.42 (s, 1H), 5.92-5.67 (br s, 1H), 4.65 (s, 1H), 4.00 (s, 1H), 3.91 (s, 1H), 1.85-1.33 (m, 17H).

Preparative Example 1.2

6-chloro-4-[(4,6-dimethylpyridin-2-yl)amino]pyridine-3-carbonitrile

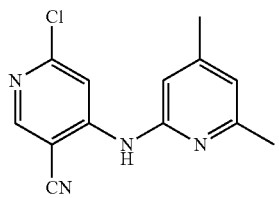 [SMILES: Cc1cc(C)nc(Nc2cc(Cl)ncc2C#N)c1]

PrepEx 1.2

A mixture of 6-chloro-4-iodopyridine-3-carbonitrile (CAS: 1061357-83-2) (5.0 g, 19 mmol), 4,6-dimethylpyridin-2-amine (2.31 g, 18.9 mmol), Xantphos (2.2 g, 3.8 mmol), Pd$_2$(dba)$_3$ (1.73 g, 1.89 mmol), and cesium carbonate (8.62 g, 26.5 mmol) was purged with nitrogen. Dioxane (45 mL) was added, and the reaction mixture was heated to 50° C. After 1 hour, the mixture was allowed to cool to room temperature, filtered through a pad of CELITE, and washed with dichloromethane. The mixture was concentrated under reduced pressure, diluted with water, and extracted with dichloromethane (2×20 mL). The organics were combined, dried over sodium sulfate, filtered, and concentrated under reduced pressure. The residue was recrystallized from ethyl acetate to provide 6-chloro-4-[(4,6-dimethylpyridin-2-yl)amino]pyridine-3-carbonitrile. MS ESI calc'd. for $C_{13}H_{12}ClN_4$ $[M+H]^+$ 259. found 259. $^1$H NMR (500 MHz, DMSO-d$_6$) δ 9.70 (s, 1H), 8.57 (s, 1H), 8.31 (s, 1H), 6.92 (s, 1H), 6.80 (s, 1H), 2.37 (s, 3H), 2.25 (s, 3H).

Preparative Example 1.3

6-chloro-4-[(6-methylpyridin-2-yl)amino]pyridine-3-carbonitrile

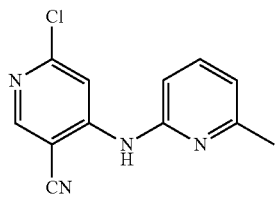

PrepEx 1.3

6-chloro-4-[(6-methylpyridin-2-yl)amino]pyridine-3-carbonitrile was prepared from 6-chloro-4-iodopyridine-3-carbonitrile using chemistry analogous to that described for 6-chloro-4-[(4,6-dimethylpyridin-2-yl)amino]pyridine-3-carbonitrile. $^1$H NMR (600 MHz, CDCl$_3$) δ 8.63 (s, 1H), 8.40

(s, 1H), 7.59 (t, J=7.8 Hz, 1H), 7.19 (s, 1H), 6.91 (d, J=7.8 Hz, 1H), 6.74 (d, J=8.4 Hz, 1H), 2.54 (s, 3H).

Preparative Example 2

Preparation of B Moiety Precursors

Preparative Example 2.1

4,6-bis(1-methyl-1H-pyrazol-4-yl)pyridin-2-amine

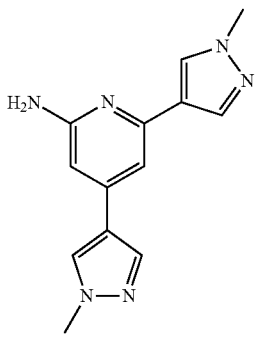 [SMILES: Cn1cc(-c2cc(N)nc(-c3cnn(C)c3)c2)cn1]

PrepEx 2.1

A mixture of 2-Boc-amino-4,6-dichloropyridine (Oakwood Products, Inc.; CAS: 1017789-38-6) (200 mg, 0.760 mmol), 1-methyl-4-(4,4,5,5-tetramethyl-1,3,2-dioxaborolan-2-yl)-1H-pyrazole (348 mg, 1.67 mmol), [1,1'-bis(diphenylphosphino)ferrocene]dichloropalladium(II) (62 mg, 0.076 mmol), and potassium phosphate tribasic (484 mg, 2.28 mmol) in a flask was evacuated and backfilled with argon three times. Dioxane (3 mL) and water (0.33 mL) were added, and the reaction mixture was heated to 100° C. for 5 hours. The mixture was allowed to cool to room temperature. Hydrochloric acid (4.0 N in dioxane, 3.80 mL, 15 mmol) was added to the mixture, and the suspension was stirred vigorously for 14 hours at room temperature. The mixture was filtered and concentrated under reduced pressure. The residue was dissolved in DMSO and purified via reverse phase HPLC (15-50% acetonitrile/water with 0.1% TFA, linear gradient) to give 4,6-bis(1-methyl-1H-pyrazol-4-yl)pyridin-2-amine. MS ESI calc'd. for $C_{13}H_{15}N_6$ [M+H]$^+$ 255. found 255. $^1$H NMR (500 MHz, DMSO-d$_6$) δ 8.46 (s, 1H), 8.42 (s, 1H), 8.15 (s, 1H), 8.11 (s, 1H), 7.70-7.59 (m, 2H), 7.40 (s, 1H), 6.80 (s, 1H), 3.93 (s, 3H), 3.90 (s, 3H).

Preparative Example 2.2

6-methyl-5-(1-methyl-1H-pyrazol-4-yl)pyridin-2-amine

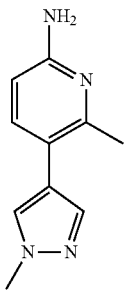

PrepEx 2.2

Dioxane (8.7 mL), 5-bromo-6-methylpyridin-2-amine (Maybridge, CAS: 42753-71-9, Cornwall, UK) (722 mg, 3.47 mmol), water (1.0 mL) and tribasic potassium phosphate (1.84 g, 8.68 mmol) were added to 1-methyl-4-(4,4,5,5-tetramethyl-1,3,2-dioxaborolan-2-yl)-1H-pyrazole (Sigma-Aldrich, CAS: 761446-44-0 St. Louis, Mo.) (541 mg, 2.89 mmol) in a scintillation vial. The vial was purged and flushed with argon 3 times before adding PdCl$_2$(dppf)-CH$_2$Cl$_2$ adduct (236 mg, 0.289 mmol). The vial was again purged and flushed 3 times with argon before sealing the vial and heating to 100° C. After 16 hours, the reaction mixture was cooled to room temperature and filtered through CELITE (washing with chloroform). The filtrate was diluted with water, and the organic layer was separated, dried over sodium sulfate, filtered, and concentrated under reduced pressure. The residue was purified by silica gel chromatography (10-100% (10% MeOH in chloroform)/hexanes, linear gradient) followed by reverse phase HPLC (5-50% acetonitrile/water with 0.1% TFA, linear gradient) to afford 6-methyl-5-(1-methyl-1H-pyrazol-4-yl)pyridin-2-amine TFA salt. MS ESI calc'd. for $C_{10}H_{13}N_4$ [M+H]$^+$ 189. found 189. $^1$H NMR (500 MHz, CD$_3$OD) δ 7.67 (s, 1H), 7.53 (s, 1H), 7.41 (d, J=8.4 Hz, 1H), 6.45 (d, J=8.4 Hz, 1H), 3.92 (s, 3H), 3.30 (s, 3H).

Preparative Example 2.3

6-(2H-1,2,3-triazol-2-yl)pyridin-2-amine

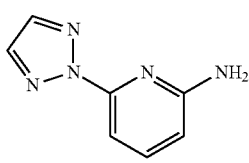 [SMILES: Nc1cccc(-n2nccn2)n1]

PrepEx 2.3

6-Chloropyridin-2-amine (2.00 g, 15.6 mmol) and 1H-1,2,3-triazole (3.22 g, 46.7 mmol) were combined in a 75 mL sealed flask and heated overnight at 180° C. The reaction mixture was cooled to room temperature, and diluted with DCM and a solution of saturated aqueous ammonium chloride. The organic layer was dried over sodium sulfate, filtered and concentrated under reduced pressure. The residue was purified by silica gel chromatography (0-50% acetone in hexanes, linear gradient) to afford a 1:1 mixture of 1H and 2H triazole regioisomers. Further purification by HPLC afforded the separated regioisomers (15-30% acetonitrile/water with 0.1% ammonium hydroxide, linear gradient). MS ESI calc'd. for $C_7H_8N_5$ $[M+H]^+$ 162. found 162. $^1$H NMR (2H isomer, 500 MHz, DMSO-$d_6$) δ 8.03 (s, 2H), 7.56 (t, J=7.9, 1H), 7.03 (d, J=7.6, 1H), 6.46 (d, J=8.1, 1H), 6.39 (s, 2H).

Preparative Example 3

Preparation of A Moiety Precursors

Preparative Example 3.1 tert-butyl [4-(aminomethyl)tetrahydro-2H-pyran-4-yl]carbamate

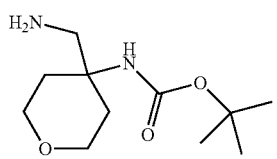 [SMILES: CC(C)(C)OC(=O)NC1(CN)CCOCC1]

PrepEx 3.1

Step 1

To a solution of tetrahydropyran-4-one (150 g, 1.50 mol) in methanol (1500 mL) was added potassium cyanide (6.0 M in water, 400 mL, 2.4 mol), ammonium hydroxide (25% solution in water, 1000 mL, 7.4 mol), and ammonium chloride (161 g, 3.00 mol). The reaction mixture was heated to 70° C. After 16 hours, the reaction mixture was cooled, quenched with cold brine (2000 mL), and extracted with dichloromethane (4×1500 mL). The organic layers were combined, dried over anhydrous magnesium sulfate, and concentrated under reduced pressure to afford 4-amino-tetrahydro-2H-pyran-4-carbonitrile. The material was used without further purification.

Step 2

To a solution of 4-amino-tetrahydro-2H-pyran-4-carbonitrile (130 g, 1.03 mol) in dichloromethane (1000 mL) was added 4-dimethylaminopyridine (252 g, 2.06 mol) followed by di-tert-butyl dicarbonate (3.33 M in dichloromethane, 300 mL, 1.03 mol) at a temperature maintained between 0-10° C. The reaction mixture was then allowed to warm to ambient temperature. After 16 hours, the reaction mixture was adjusted to pH ~7 by the addition of hydrochloric acid (10% aqueous solution). The reaction mixture was extracted with dichloromethane (3×800 mL). The organics were combined, washed with brine (600 mL), dried over magnesium sulfate, and concentrated under reduced pressure. The residue was purified via chromatography on silica gel (4-12% ethyl acetate/petroleum ether, linear gradient) to afford tert-butyl (4-cyanotetrahydro-2H-pyran-4-yl)carbamate.

Step 3

A mixture of tert-butyl (4-cyanotetrahydro-2H-pyran-4-yl)carbamate (59 g, 260 mmol) and Raney Nickel (25 g) in isopropanol and ammonia (700 mL) was stirred under a hydrogen atmosphere. After 36 hours, the solids were filtered and the filtrate was concentrated under reduced pressure. The residue was recrystallized from DCM (60 mL) to afford tert-butyl [4-(aminomethyl)tetrahydro-2H-pyran-4-yl]carbamate. MS ESI calc'd. for $C_{11}H_{23}N_2O_3$ $[M+H]^+$ 231. found 231. $^1$H NMR (400 MHz, CDCl$_3$) δ 4.42 (s, 1H), 3.77 (d, J=11.6 Hz, 2H), 3.66-3.60 (m, 2H), 2.94 (s, 2H), 1.97-1.94 (d, J=13.6 Hz, 2H), 1.57 (m, 2H), 1.44 (s, 9H), 1.28 (s, 2H).

Preparative Example 3.2 tert-butyl [3-(aminomethyl)tetrahydrofuran-3-yl]carbamate

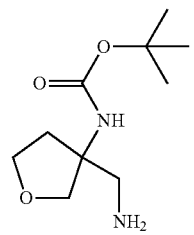

PrepEx 3.2

Step 1

To neat butane-1,2,4-triol (300 g, 2.83 mol) was added 4-methylbenzenesulfonic acid (10 g, 58 mmol). The reaction mixture was heated to 180° C. After 2 hours, the reaction mixture was cooled to ambient temperature and tetrahydrofuran-3-ol was afforded by distillation of the mixture under reduced pressure (10 mm Hg; the product fraction was collected at 46° C.).

Step 2

To a solution of tetrahydrofuran-3-ol (92.5 g, 1.05 mol) in dichloromethane (2000 mL) was added pyridinium chlorochromate (454 g, 2.10 mol) and silicon gel (500 g). The reaction mixture was heated to 40° C. After 16 hours, the reaction mixture was filtered, and the filtrate was concentrated under reduced pressure to afford the crude residue. The residue was purified via chromatography on silica gel (methanol/DCM, linear gradient) to afford dihydrofuran-3(2H)-one.

Step 3

To a solution of dihydrofuran-3(2H)-one (10.0 g, 116 mmol) in ammonia (solution in methanol, 100 mL) at 0° C. was added acetic acid (7.67 g, 128 mmol) followed by potassium cyanide (7.56 g, 116 mmol). The reaction mixture was heated to 50° C. After 2 hours, the reaction mixture was cooled to ambient temperature and concentrated under reduced pressure to afford the crude residue. The residue was diluted with aqueous iron sulfate (100 mL) and extracted with ethyl acetate (3×20 mL). The organics were combined, dried over anhydrous sodium sulfate, and concentrated under reduced pressure to afford 3-aminotetrahydrofuran-3-carbonitrile. The material was used without purification.

Step 4

To neat 3-aminotetrahydrofuran-3-carbonitrile (56 g, 500 mmol) was added di-tert-butyl dicarbonate (200 g, 917 mmol). The reaction mixture was heated to reflux. After 2 hours, the reaction mixture was cooled to ambient temperature and concentrated under reduced pressure. The residue was purified via chromatography on silica gel (20% ethyl acetate/petroleum ether) to afford tert-butyl (3-cyanotetrahydrofuran-3-yl)carbamate.

Step 5

A mixture of tert-butyl (3-cyanotetrahydrofuran-3-yl)carbamate (80.0 g, 377 mmol) and Raney Nickel (20 g) in ammonia (solution in methanol, 500 mL) was stirred at ambient temperature under a hydrogen atmosphere. After 16 hours, the reaction mixture was decanted and the residual Raney Nickel was washed with methanol. The reaction mixture was filtered through silica gel and concentrated under reduced pressure. The residue was diluted with ethanol (1000 mL) followed by oxalic acid dropwise (1.3 M solution in ethanol, 200 mL, 260 mmol), and then concentrated under reduced pressure. The residue was diluted with diethyl ether (1000 mL) and filtered. This isolated solids were dried under reduced pressure to afford tert-butyl [3-(aminomethyl)tetrahydrofuran-3-yl]carbamate oxalic acid salt. MS ESI calc'd. for $C_{10}H_{21}N_2O_3$ $[M+H]^+$ 217. found 217. $^1$H NMR (300 MHz, CDCl$_3$) δ 3.96-3.81 (m, 4H), 3.40 (d, J=12.9 Hz, 1H), 3.22 (d, J=12.9 Hz, 1H), 2.18-2.07 (m, 2H), 1.48 (s, 9H).

Preparative Example 3.3

3,3,3-trifluoropropane-1,2-diamine

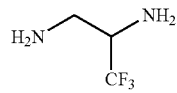

PrepEx 3.3

Step 1

To a solution of ethyl 3,3,3-trifluoro-2-oxopropanoate (1500 g, 8.82 mol) in dichloromethane (5000 mL) was added benzyl carbamate (1330 g, 8.82 mol). After 2 days, the reaction mixture was filtered to afford ethyl N-[(benzyloxy)carbonyl]-3,3,3-trifluoro-2-hydroxyalaninate. The material was used without further purification.

Step 2

To a solution of ethyl N-[(benzyloxy)carbonyl]-3,3,3-trifluoro-2-hydroxyalaninate (2690 g, 8.39 mol) in diethyl ether (18 L) under an atmosphere of nitrogen was added dropwise 2,2,2-trifluoroacetyl 2,2,2-trifluoroacetate (1937 g, 9.22 mol) at 0° C. followed by the addition of pyridine dropwise (1457 g, 18.44 mol) at 0° C. The reaction mixture was allowed to warm to ambient temperature. After 6 hours, the reaction mixture was filtered, and the filtrate was concentrated under reduced pressure to afford ethyl (2E)-2-{[(benzyloxy)carbonyl]imino}-3,3,3-trifluoropropanoate.

Step 3

To a solution of ethyl (2E)-2-{[(benzyloxy)carbonyl]imino}-3,3,3-trifluoropropanoate (2500 g, 8.25 mol) in diethyl ether (15 L) under a nitrogen atmosphere was added sodium borohydride (627 g, 16.5 mol) in several batches at 0° C. The reaction mixture was allowed to warm to ambient temperature. After 16 hours, the reaction mixture was quenched with water (500 mL) and extracted with ethyl acetate (3×2000 mL). The organic layers were combined, washed with brine (2×500 mL), dried over anhydrous sodium sulfate, and concentrated under reduced pressure. The residue was purified via chromatography on silica gel (10% ethyl acetate/petroleum ether) to afford ethyl N-[(benzyloxy)carbonyl]-3,3,3-trifluoroalaninate.

Step 4

To a suspension of calcium chloride (2885 g, 26.23 mol) in diethyl ether (8 L) under a nitrogen atmosphere was added sodium borohydride (1993 g, 52.45 mol). To this mixture was added dropwise ethyl N-[(benzyloxy)carbonyl]-3,3,3-trifluoroalaninate (3.28 M solution in diethyl ether, 2000 mL, 6.56 mol) at 0° C. The reaction mixture was allowed to warm to ambient temperature. After 16 hours, reaction mixture was quenched with water (10 L) and extracted with ethyl acetate (3×2000 mL). The organic layers were combined, washed with brine (2×500 mL), dried over anhydrous sodium sulfate, and concentrated under reduced pressure. The residue was purified via chromatography on silica gel (10% ethyl acetate/petroleum ether) to afford benzyl (1,1,1-trifluoro-3-hydroxypropan-2-yl)carbamate.

Step 5

To a solution of benzyl (1,1,1-trifluoro-3-hydroxypropan-2-yl)carbamate (300 g, 1.14 mol) in dichloromethane (2500 mL) were added triethylamine (128 g, 1.27 mol) and methanesulfonylchloride (144 g, 1.26 mol). After 2 hours, the reaction mixture was quenched with water (1000 mL) and extracted with dichloromethane (3×300 mL). The organic layers were combined, dried over anhydrous sodium sulfate, and concentrated under reduced pressure to afford 2-{[(benzyloxy)carbonyl]amino}-3,3,3-trifluoropropyl methanesulfonate. The material was used without further purification.

Step 6

To a solution of 2-{[(benzyloxy)carbonyl]amino}-3,3,3-trifluoropropyl methanesulfonate (213 g, 625 mmol) in DMF (2500 mL) was added sodium azide (91.1 g, 1.40 mol). The reaction mixture was heated to 80° C. After 16 hours, the reaction mixture was diluted with water (1000 mL) and extracted with ethyl acetate (3×500 mL). The organics were combined, dried over anhydrous sodium sulfate, and concentrated under reduced pressure. The residue was purified via chromatography on silica gel (10% ethyl acetate/petroleum ether) to afford benzyl (3-azido-1,1,1-trifluoropropan-2-yl)carbamate.

Step 7

To a solution of benzyl (3-azido-1,1,1-trifluoropropan-2-yl)carbamate (120 g, 417 mmol) in methanol (1000 mL)

under a nitrogen atmosphere was added palladium on carbon (10% w/w, 13 g). The reaction mixture was purged with hydrogen gas and then stirred under a hydrogen atmosphere. After 16 hours, the reaction mixture was filtered, and the filtrate was concentrated under reduced pressure to afford 3,3,3-trifluoropropane-1,2-diamine. The material was used without further purification.

Step 8

To neat 3,3,3-trifluoropropane-1,2-diamine (43 g, 340 mmol) was added hydrochloric acid (36% solution in water, 100 mL). After 16 hours, the reaction mixture was concentrated under reduced pressure to afford 3,3,3-trifluoropropane-1,2-diamine hydrochloric acid salt. MS ESI calc'd. for $C_3H_8F_3N_2$ [M+H]$^+$ 129. found 129. $^1$H NMR (300 MHz, D$_2$O) δ 4.49-4.41 (m, 1H), 3.65-3.58 (m, 1H), 3.48-3.42 (m, 1H).

Preparative Example 3.4 trans-tetrahydrofuran-3,4-diamine

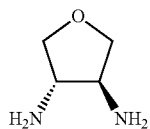

PrepEx 3.4

Step 1

To a solution of 3,4-epoxytetrahydrofuran (57.4 g, 0.67 mol) in ethanol (344 mL) was added diallylamine (194 g, 2.00 mol). The reaction mixture was heated to 75° C. After 2 days, the reaction mixture was cooled and concentrated under reduced pressure to afford trans-4-(diprop-2-en-1-ylamino) tetrahydrofuran-3-ol. The material was used without further purification.

Step 2

To a solution of trans-4-(diprop-2-en-1-ylamino)tetrahydrofuran-3-ol (50.0 g, 0.273 mol) in methyl tert-butyl ether was added triethylamine (44.0 g, 0.437 mol) at 5° C. Methanesulfonyl chloride (25.4 mL, 0.327 mol) was added using an addition funnel over a period of 15 min at 5° C. After 30 minutes, triethylamine (55.0 g, 0.546 mol) was added and the reaction was allowed to warm to ambient temperature. Ammonium hydroxide (29% aqueous solution, 700 mL) was then added. After 16 hours, the organic layer was separated, and the aqueous layer was washed with methyl tert-butyl ether (3×250 mL). The organic layers were combined, washed with brine, dried over sodium sulfate, and concentrated under reduced pressure to afford adduct trans-N,N-di (prop-2-en-1-yl)tetrahydrofuran-3,4-diamine. The material was used without further purification.

Step 3

To a solution of trans-N,N-di(prop-2-en-1-yl)tetrahydrofuran-3,4-diamine (37.6 g, 0.20 mol) in THF (376 mL) was added sodium carbonate (1.0 M solution in water, 300 mL, 0.30 mol). The reaction mixture was cooled to 0-5° C. and di-tert-butyl dicarbonate (66 g, 0.30 mol) was added. The reaction mixture was then allowed to warm to ambient temperature. After 16 hours, the reaction mixture was diluted with water (800 mL) and the organic layer was separated. The aqueous layer was extracted with methyl tert-butyl ether (3×250 mL), and the organic layers were combined, washed with brine, dried over sodium sulfate, and concentrated under reduced pressure to afford tert-butyl [trans-4-(diprop-2-en-1-ylamino)tetrahydrofuran-3-yl]carbamate. The material was used without further purification.

Step 4

To a suspension of N,N-dimethylbarbituric acid (86.9 g, 0.557 mol) and tetrakis(triphenylphosphine)palladium(0) (5.5 g, 4.8 mmol) in dichloromethane (450 mL) was added tert-butyl [trans-4-(diprop-2-en-1-ylamino)tetrahydrofuran-3-yl]carbamate under a nitrogen atmosphere. The reaction mixture was heated to 35° C. After 90 minutes, the reaction mixture was cooled to ambient temperature and concentrated under reduced pressure. The residue was dissolved in methyl tert-butyl ether (1000 mL) and washed with saturated aqueous sodium carbonate solution (800 mL). The organic layer was separated and treated with Darco G60 carbon (8.0 g), filtered, and diluted with hydrochloric acid (2.9 M in isopropyl acetate, 250 mL, 730 mmol). After 16 hours, the mixture was filtered to afford the crude residue. The residue was suspended in a hydrochloric acid (0.4 N in water, 2500 mL, 1 mol) and heated to 60° C. The mixture was filtered, and the filtrate was washed with DCM (500 mL). The aqueous layer was partially concentrated under reduced pressure to a volume of 150-200 mL, and then diluted with methyl tert-butyl ether (200 mL) and ethanol (50 mL). The mixture was cooled to 0° C., and after 30 minutes the solids were filtered, washed with methyl tert-butyl ether, and dried under reduced pressure to afford trans-tetrahydrofuran-3,4-diamine hydrochloric acid salt. MS ESI calc'd. for $C_4H_{11}N_2O$ [M+H]$^+$ 103. found 103. $^1$H NMR (300 MHz, DMSO-d$_6$) δ 8.84 (s, 6H), 4.16-4.11 (m, 2H), 3.91-3.88 (m, 2H), 3.82-3.76 (m, 2H).

Preparative Example 3.5 benzyl [(2R)-1-amino-3-methoxypropan-2-yl]carbamate

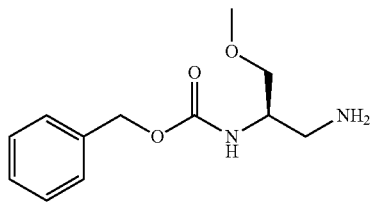 [SMILES: COC[C@@H](CN)NC(=O)OCc1ccccc1]

PrepEx 3.5

Step 1

To a solution of N-[(benzyloxy)carbonyl]-L-serine (70 g, 0.29 mol) in acetonitrile (1.2 L) was added iodomethane (208 g, 1.46 mol) and silver oxide (203 g, 0.88 mol). After 16 hours, the reaction mixture was filtered, and the filtrate was concentrated under reduced pressure. The residue was purified via chromatography on silica gel (6% ethyl acetate/petroleum ether) to give methyl N-[(benzyloxy)carbonyl]-O-methyl-L-serinate. MS ESI calc'd. for $C_{13}H_{18}NO_5$ [M+H]$^+$ 268. found 268. $^1$H NMR (400 MHz, CDCl$_3$) δ 7.37-7.31 (m, 5H), 5.63 (d, J=8.0 Hz, 1H), 5.13 (s, 2H), 4.51-4.47 (m, 1H), 3.84-3.81 (m, 1H), 3.77 (s, 3H), 3.63-3.60 (m, 1H), 3.33 (s, 3H).

Step 2

To a solution of methyl N-[(benzyloxy)carbonyl]-O-methyl-L-serinate (60 g, 0.22 mol) in methanol (600 mL) was added lithium borohydride (39.2 g, 1.80 mol). After 2 hours, the reaction mixture was quenched with saturated aqueous ammonium chloride solution, partially concentrated under reduced pressure, and diluted with water. The mixture was extracted with ethyl acetate (3×100 mL), and the combined organic layers were dried over sodium sulfate and concentrated under reduced pressure. The residue was purified via chromatography on silica gel to give benzyl [(2R)-1-hydroxy-3-methoxypropan-2-yl]carbamate. MS ESI calc'd. for $C_{12}H_{18}NO_4$ [M+H]$^+$ 240. found 240. $^1$H NMR (400 MHz, CDCl$_3$) δ 7.56-7.30 (m, 5H), 5.52 (br s, 1H), 5.08 (s, 2H), 3.84 (d, J=16.0 Hz, 2H), 3.76-3.64 (m, 1H), 3.63-3.52 (m, 2H), 3.38 (s, 3H), 2.55 (bs, 1H).

Step 3

To a solution of benzyl [(2R)-1-hydroxy-3-methoxypropan-2-yl]carbamate (30 g, 0.13 mol) in DCM (300 mL) at 0° C. was added triethylamine (19.0 g, 0.188 mol) and methanesulfonylchloride (21.6 g, 0.188 mol) and then the reaction mixture was allowed to warm to ambient temperature. After 16 hours, the reaction mixture was washed with brine, and the organics were dried over sodium sulfate and concentrated under reduced pressure. The residue was purified via chromatography on silica gel (10% ethyl acetate/petroleum ether) to give (2S)-2-{[(benzyloxy)carbonyl]amino}-3-methoxypropyl methanesulfonate. MS ESI calc'd. for $C_{13}H_{20}NO_6S$ [M+H]$^+$ 318. found 318. $^1$H NMR (400 MHz, CDCl$_3$) δ 7.36-7.33 (m, 5H), 5.24 (d, J=8.0 Hz, 1H), 5.10 (s, 2H), 4.28 (d, J=5.6 Hz, 2H), 4.12-4.09 (m, 1H), 3.55-3.42 (m, 2H), 3.35 (s, 3H), 2.99 (s, 3H).

Step 4

To a solution of (2S)-2-{[(benzyloxy)carbonyl]amino}-3-methoxypropyl methanesulfonate (37.6 g, 0.118 mol) in DMF (400 mL) was added sodium azide (23.2 g, 0.178 mol) and tetrabutylammonium iodide (0.526 g, 1.42 mmol), and then the reaction mixture was heated to 80° C. After 3 hours, the reaction mixture was cooled to ambient temperature, diluted with saturated aqueous sodium bicarbonate, and extracted with ethyl acetate. The organic layer was dried over sodium sulfate and concentrated under reduced pressure. The residue was diluted with THF/water (250 mL/50 mL), and to this mixture was added triphenylphospine (36.7 g, 0.140 mol). After 2 hours, the reaction mixture was diluted with water and extracted with ethyl acetate (6×300 mL). The combined organic layers were dried over sodium sulfate and concentrated under reduced pressure. The residue was purified via chromatography on silica gel (3% methanol/DCM) to afford benzyl [(2R)-1-amino-3-methoxypropan-2-yl]carbamate. MS ESI calc'd. for $C_{12}H_{19}N_2O_3$ [M+H]$^+$ 239. found 239. $^1$H NMR (400 MHz, CDCl$_3$) δ 7.46-7.39 (m, 5H), 5.86 (d, J=7.2 Hz, 1H), 5.12-5.05 (m, 2H), 3.92 (bs, 1H), 3.55-3.49 (m, 2H), 3.34 (s, 3H), 2.93 (d, J=5.6 Hz, 2H), 1.91 (s, 2H).

Additional A moiety precursors are prepared using the published procedures which are specified below.

Tert-butyl (1R,2R)-2-amino-3,3-difluorocyclohexylcarbamate was prepared according to the procedures described at pages 51-54 in International Patent Application Publication No. WO 2010/017046. Similarly, the enantiomer, tert-butyl (1S,2S)-2-amino-3,3-difluorocyclohexylcarbamate was prepared analogously.

Tert-butyl [(3R,4R)-4-aminotetrahydro-2H-pyran-3-yl]carbamate is prepared according to the procedures described at pages 32-39 of International Patent Application Publication No. WO 2010/097248.

Example 1

Conversions from Scheme 1—Conversion of A1 to Structural Type A

Example 1.1

6-{[(1R,2S)-2-aminocyclohexyl]amino}-4-{[6-(trifluoromethyl)pyridin-2-yl]amino}pyridine-3-carboxamide

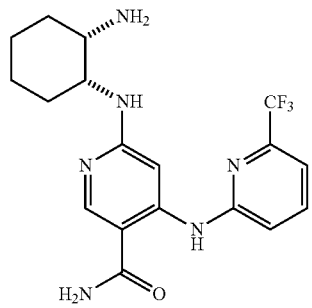

1.1

Step 1

A mixture of tert-butyl {(1S,2R)-2-[(4-chloro-5-cyanopyridin-2-yl)amino]cyclohexyl}carbamate (PrepEx 1.1) (80 mg, 0.23 mmol), 2-amino-6-(trifluoromethyl)pyridine (37 mg, 0.23 mmol), 2-dicyclohexylphosphino-2',4',6'-triisopropylbiphenyl (16 mg, 0.034 mmol), Pd$_2$(dba)$_3$ (21 mg, 0.023 mmol), and cesium carbonate (149 mg, 0.456 mmol) in a flask was evacuated and backfilled with nitrogen (3×). Dioxane (1.5 mL) was added, and the reaction mixture was heated to 80° C. for 3 hours. The mixture was allowed to cool to room temperature. TFA (0.386 mL, 5.02 mmol) was added, and the suspension was heated to 65° C. for 14 hours. The mixture was allowed to cool to room temperature, filtered, and concentrated under reduced pressure. The residue was dissolved in DMSO, filtered, and purified via reverse phase HPLC (acetonitrile/water with 0.1% TFA, linear gradient) to afford 6-[(1R,2S)-2-aminocyclohexyl]amino}-4-{[6-(trifluoromethyl)pyridin-2-yl]amino}pyridine-3-carbonitrile. MS ESI calc'd. for $C_{18}H_{20}F_3N_6$ [M+H]$^+$ 377. found 377.

Step 2

6-[(1R,2S)-2-aminocyclohexyl]amino}-4-{[6-(trifluoromethyl)pyridin-2-yl]amino}pyridine-3-carbonitrile (47 mg, 0.096 mmol) was dissolved in DMSO (1.5 mL). Potassium hydroxide (27 mg, 0.48 mmol) and hydrogen peroxide (35% solution in water, 0.084 mL, 0.96 mmol) were added sequentially, and the reaction mixture was stirred for 1 hour at room temperature. The reaction mixture was filtered and purified via reverse phase HPLC (acetonitrile/water with 0.1% TFA, linear gradient) to give 6-{[(1R,2S)-2-aminocyclohexyl]amino}-4-{[6-(trifluoromethyl)pyridin-2-yl]amino}pyridine-3-carboxamide. MS ESI calc'd. for $C_{18}H_{22}F_3N_6O$ [M+H]$^+$ 395. found 395. $^1$H NMR (500 MHz, DMSO-$d_6$) 12.45-12.23 (m, 1H), 8.56 (s, 1H), 8.36-8.24 (m, 1H), 8.02 (s, 1H), 8.10-7.62 (m, 5H), 7.55 (d, J=8.0 Hz, 1H), 7.38 (d, J=7.8 Hz, 1H), 4.12-3.92 (m, 1H), 3.53-3.47 (m, 1H), 1.94-1.77 (m, 2H), 1.74-1.52 (m, 4H), 1.46-1.34 (m, 2H).

The following compounds in Table A were prepared using procedures which were analogous to those described above in Example 1.1

TABLE A

| Ex. No. | A | B | Name | [M + H]$^+$ Calc'd | [M + H]$^+$ Obsv'd | Form |
|---|---|---|---|---|---|---|
| 1.2 | (1R,2S)-2-aminocyclohexyl | 6-methylpyridin-2-yl | 6-{[(1R,2S)-2-aminocyclohexyl]amino}-4-[(6-methylpyridin-2-yl)amino]pyridine-3-carboxamide | 341 | 341 | TFA Salt |
| 1.3 | 2-aminoethyl | 6-methylpyridin-2-yl | 6-[(2-aminoethyl)amino]-4-[(6-methylpyridin-2-yl)amino]pyridine-3-carboxamide | 287 | 287 | TFA Salt |
| 1.4 | (1R,2S)-2-aminocyclohexyl | 6-(2H-1,2,3-triazol-2-yl)pyridin-2-yl | 6-{[(1R,2S)-2-aminocyclohexyl]amino}-4-{[6-(2H-1,2,3-triazol-2-yl)pyridin-2-yl]amino}pyridine-3-carboxamide | 394 | 394 | TFA Salt |
| 1.5 | (1R,2S)-2-aminocyclohexyl | 4,6-dimethylpyridin-2-yl | 6-{[(1R,2S)-2-aminocyclohexyl]amino}-4-[(4,6-dimethylpyridin-2-yl)amino]pyridine-3-carboxamide | 355 | 355 | TFA Salt |
| 1.6 | (1R,2S)-2-aminocyclohexyl | quinolin-2-yl | 6-{[(1R,2S)-2-aminocyclohexyl]amino}-4-(quinolin-2-ylamino)pyridine-3-carboxamide | 377 | 377 | TFA Salt |
| 1.7 | (1R,2S)-2-aminocyclohexyl | 5-fluoro-6-methylpyridin-2-yl | 6-{[(1R,2S)-2-aminocyclohexyl]amino}-4-[(5-fluoro-6-methylpyridin-2-yl)amino]pyridine-3-carboxamide | 359 | 359 | TFA Salt |

TABLE A-continued

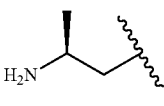

| Ex. No. | A | B | Name | [M + H]+ Calc'd | [M + H]+ Obsv'd | Form |
|---|---|---|---|---|---|---|
| 1.8 | 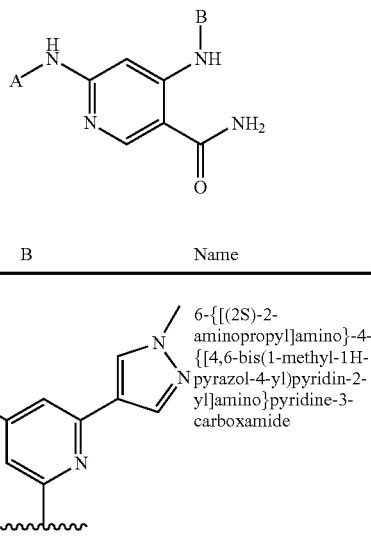 | 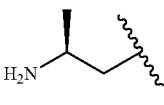 | 6-{[(2S)-2-aminopropyl]amino}-4-{[4,6-bis(1-methyl-1H-pyrazol-4-yl)pyridin-2-yl]amino}pyridine-3-carboxamide | 447 | 447 | TFA Salt |
| 1.9 | 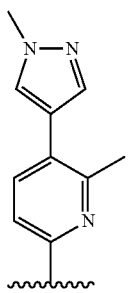 | 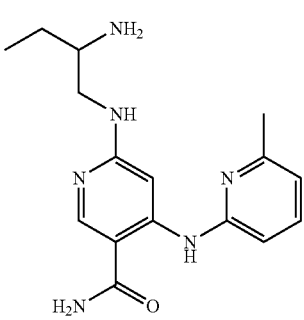 | 6-{[(2S)-2-aminopropyl]amino}-4-{[6-methyl-5-(1-methyl-1H-pyrazol-4-yl)pyridin-2-yl]amino}pyridine-3-carboxamide | 381 | 381 | TFA Salt |

Example 2

Conversion of A5 to Structural Subtype A

Example 2.1

6-[(2-aminobutyl)amino]-4-[(6-methylpyridin-2-yl)amino]pyridine-3-carboxamide

Step 1

To a solution of 6-chloro-4-[(6-methylpyridin-2-yl)amino]pyridine-3-carbonitrile (PrepEx 1.3) (38 mg, 0.16 mmol) in NMP (1 mL) was added butane-1,2-diamine (107 mg, 1.21 mmol) and N,N-diisopropylethylamine (0.163 mL, 0.932 mmol). The reaction mixture was heated to 100° C. After 16 hours, the reaction mixture was allowed to cool to room temperature, filtered, and purified directly via reverse phase HPLC (acetonitrile/water with 0.1% TFA, linear gradient) to afford 6-[(2-aminobutyl)amino]-4-[(6-methylpyridin-2-yl)amino]pyridine-3-carbonitrile. MS ESI calc'd. for $C_{16}H_{21}N_6$ $[M+H]^+$ 297. found 297.

Step 2

To a solution of 6-[(2-aminobutyl)amino]-4-[(6-methylpyridin-2-yl)amino]pyridine-3-carbonitrile (24 mg, 0.081 mmol) in DMSO (1 mL) was added hydrogen peroxide (35% aqueous solution, 0.071 mL, 0.81 mmol) and potassium hydroxide (45 mg, 0.81 mmol). The reaction mixture was stirred for 16 hours, and then was filtered and purified directly via reverse phase HPLC (acetonitrile/water with 0.1% TFA, linear gradient) to afford 6-[(2-aminobutyl)amino]-4-[(6-methylpyridin-2-yl)amino]pyridine-3-carboxamide. MS ESI calc'd. for $C_{16}H_{23}N_6O$ $[M+H]^+$ 315. found 315. $^1$H NMR (500 MHz, CD$_3$OD) δ 8.34 (s, 1H), 7.79 (s, 1H), 7.55 (t, J=8.0 Hz, 1H), 6.80 (d, J=7.5 Hz, 1H), 6.73 (d, J=8.0 Hz, 1H), 3.39 (dd, J=14 Hz, J=4.5 Hz, 1H), 3.18 (dd, J=13.5 Hz, J=8.0 Hz, 1H), 2.96-2.90 (m, 1H), 2.49 (s, 3H), 1.66-1.56 (m, 1H), 1.46-1.38 (m, 1H), 1.01 (t, J=7.5 Hz, 3H).

The following compounds in Table B were prepared using procedures which were analogous to those described above in Example 2.1

TABLE B

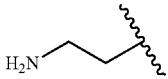

| Ex. No. | A | B | Name | [M + H] Calc'd | [M + H] Obsv'd | Form(s) |
|---|---|---|---|---|---|---|
| 2.2 | 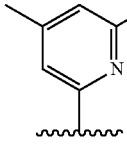 | 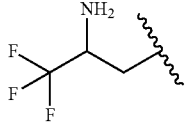 | 6-[(2-aminoethyl)amino]-4-[(4,6-dimethylpyridin-2-yl)amino]pyridine-3-carboxamide | 301 | 301 | TFA Salt |
| 2.3 | 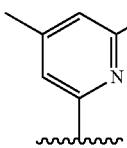 RACEMIC | 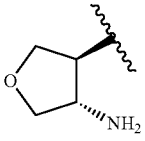 [SMILES: *[C@@H]1COC[C@H]1N] | 6-[(2-amino-3,3,3-trifluoropropyl)amino]-4-[(4,6-dimethylpyridin-2-yl)amino]pyridine-3-carboxamide | 369 | 369 | Free Base, TFA Salt |
| 2.4 | 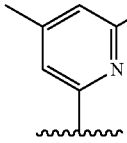 RACEMIC, TRANS | 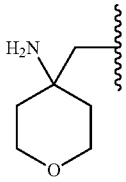 | rel-6-{[(3S,4S)-4-aminotetrahydrofuran-3-yl]amino}-4-[(4,6-dimethylpyridin-2-yl)amino]pyridine-3-carboxamide | 343 | 343 | TFA Salt |
| 2.5 | 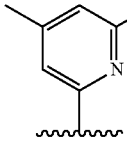 | 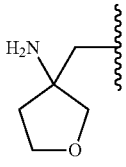 | 6-{[(4-aminotetrahydro-2H-pyran-4-yOmethyl]amino}-4-[(4,6-dimethylpyridin-2-yl)amino]pyridine-3-carboxamide | 371 | 371 | TFA Salt |
| 2.6 | 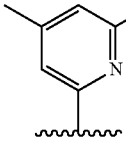 RACEMIC | 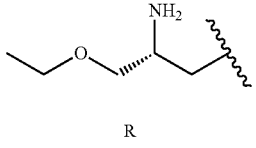 | 6-{[(3-aminotetrahydrofuran-3-yl)methyl]amino}-4-[(4,6-dimethylpyridin-2-yl)amino]pyridine-3-carboxamide | 357 | 357 | TFA Salt |
| 2.7 | 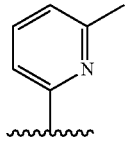 [SMILES: *c1cccc(C)n1] R | 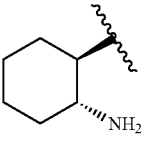 | 6-{[(2R)-2-amino-3-methoxypropyl]amino}-4-[(6-methylpyridin-2-yl)amino]pyridine-3-carboxamide | 331 | 331 | TFA Salt |
| 2.8 | 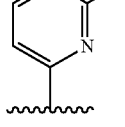 RACEMIC, TRANS | 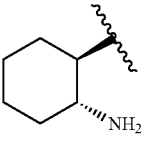 | rel-6-{[(1R,2R)-2-aminocyclohexyl]amino}-4-[(6-methylpyridin-2-yl)amino]pyridine-3-carboxamide | 341 | 341 | TFA Salt |

TABLE B-continued

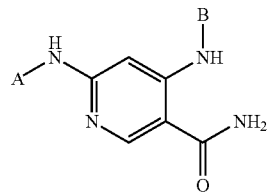

| Ex. No. | A | B | Name | [M + H] Calc'd | [M + H] Obsv'd | Form(s) |
|---|---|---|---|---|---|---|
| 2.9 | (structure) RACEMIC | (structure) | 6-[(2-amino-2-methylbutyl)amino]-4-[(6-methylpyridin-2-yl)amino]pyridine-3-carboxamide | 329 | 329 | TFA Salt |
| 2.10 | (structure) RACEMIC | (structure) | 6-[(2-amino-1-methylethyl)amino]-4-[(4,6-dimethylpyridin-2-yl)amino]pyridine-3-carboxamide | 315 | 315 | TFA Salt |
| 2.11 | (structure) RACEMIC | (structure) | 6-[(2-aminopentyl)amino]-4-[(6-methylpyridin-2-yl)amino]pyridine-3-carboxamide | 329 | 329 | Free Base |
| 2.12 | (structure) RACEMIC | (structure) | 6-[(2-amino-2-cyclopropylethyl)amino]-4-[(6-methylpyridin-2-yl)amino]pyridine-3-carboxamide | 327 | 327 | Free Base |
| 2.13 | (structure) | (structure) | 6-[(2-aminoethyl)amino]-4-[(5-bromo-6-methylpyridin-2-yl)amino]pyridine-3-carboxamide | 365, 367 | 365, 367 | TFA Salt |

Example 3

Example 3.1

6-{[(2S)-2-aminopropyl]amino}-4-[(4,6-dimethylpyridin-2-yl)amino]pyridine-3-carboxamide

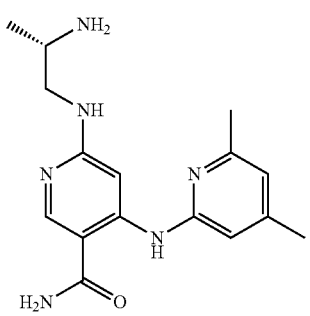

3.1

To a solution of 6-chloro-4-[(4,6-dimethylpyridin-2-yl)amino]pyridine-3-carbonitrile (PrepEx 1.2) (50 mg, 0.19 mmol) in 1,4-dioxane (0.8 mL) was added tert-butyl [(2S)-1-aminopropan-2-yl]carbamate hydrochloride (61 mg, 0.29 mmol) and cesium carbonate (126 mg, 0.387 mmol). The mixture was purged with argon, and then $Pd_2(dba)_3$ (4 mg, 0.004 mmol) and Xantphos (7 mg, 0.012 mmol) were added. The reaction mixture was heated to 80° C. After complete consumption of starting material (as determined by LCMS analysis), the reaction mixture was cooled to ambient temperature, filtered through CELITE (washed with chloroform), and diluted with water. The organics were separated, dried over anhydrous sodium sulfate, filtered, and concentrated under reduced pressure. The residue was purified by silica gel chromatography (10-40% acetone/hexanes, linear gradient) to afford tert-butyl [(2S)-1-({5-cyano-4-[(4,6-dimethylpyridin-2-yl)amino]pyridin-2-yl}amino)propan-2-yl]carbamate. The isolated material was diluted with hydrochloric acid (2.0 M in dioxanes, 1 mL, 2 mmol) and stirred at ambient temperature. After 1 hour, the reaction mixture was concentrated under reduced pressure (azeotroping with toluene). The residue was diluted with DMSO (0.5 mL). To this mixture was added hydrogen peroxide (35% solution in water, 0.020 mL, 0.23 mmol) and sodium hydroxide (4.0 N in water, 0.050 mL, 0.20 mmol). After 1 hour, the reaction mixture was filtered and purified directly by reverse phase HPLC (5-60% acetonitrile/water with 0.1% TFA, linear gradient) to afford 6-{[(2S)-2-aminopropyl]amino}-4-[(4,6-dimethylpyridin-2-yl)amino]pyridine-3-carboxamide TFA salt. MS ESI calc'd. for $C_{16}H_{23}N_6O$ $[M+H]^+$ 315. found 315. $^1H$ NMR (500 MHz, $CD_3OD$) δ 8.37 (s, 1H), 8.28 (s, 1H), 6.90 (s, 1H), 6.80 (s, 1H), 3.74-3.50 (m, 3H), 2.51 (s, 3H), 2.34 (s, 3H), 1.41 (br s, 3H).

The following compounds in Table C were prepared using procedures which were analogous to those described above in Example 3.1.

TABLE C

| Ex. No. | A | B | Name | $[M + H]^+$ Calc'd | $[M + H]^+$ Obsv'd | Form(s) |
|---|---|---|---|---|---|---|
| 3.2 | (1R,6R) difluorocyclohexyl-NH₂ | 4,6-dimethylpyridin-2-yl | 6-{[(1R,6R)-6-amino-2,2-difluorocyclohexyl]amino}-4-[(4,6-dimethylpyridin-2-yl)amino]pyridine-3-carboxamide | 391 | 391 | TFA Salt |
| 3.3 | (1S,6S) difluorocyclohexyl-NH₂ | 4,6-dimethylpyridin-2-yl | 6-{[(1S,6S)-6-amino-2,2-difluorocyclohexyl]amino}-4-[(4,6-dimethylpyridin-2-yl)amino]pyridine-3-carboxamide | 391 | 391 | TFA Salt |

Biological Assay

Homogeneous Time-Resolved Fluorescence (HTRF) Assay for the Recombinant Human Syk Enzyme A recombinant GST-hSYK fusion protein was used to measure potency of compounds to inhibit human Syk activity. The recombinant human GST-SYK (Carna Biosciences #08-176) (5 pM final concentration) was incubated with various concentrations of the inhibitor diluted in DMSO (0.1% final concentration) for 10 minutes at room temperature in 15 mM Tris-HCl (pH 7.5), 0.01% tween 20, 2 mM DTT in 384 well plate format. To initiate the reaction the biotinylated substrate peptide (250 nM final concentration) that contains the phosphorylation site for Syk was added with magnesium (5 mM final concentration) and ATP (25 μM final concentration). Final volume of the reaction was 10 μL. Phosphorylation of the peptide was allowed to proceed for 45' at room temperature. To quench the reaction and detect the phosphorylated product, 2 nM of a Europium-anti-phosphotyrosine antibody (Perkin Elmer #AD0161) and 70 nM SA-APC (Perkin-Elmer #CR130-100) were added together in 15 mM Tris pH 7.5, 40 mM EDTA, 0.01% tween 20. Final volume of the quenching solution was 10 μL. The resulting HTRF signal was measured after 30 minutes on an EnVision (Perkin-Elmer) reader using a time-resolved fluorescence protocol. $IC_{50}$ was determined following 10-dose titration (10 μM to 0.508 nM) and four parameter logistic curve fitting using an assay data analyzer. Table 1 below lists activity for representative compounds of the invention whereby the $IC_{50}$ values are rated "A" for $IC_{50}$ values <10 nM, "B" for $IC_{50}$ values between 10 nM and 100 nM, "C" for $IC_{50}$ values between 100 nM and 1,000 nM, and "D" for $IC_{50}$ values between 1,000 nM and 10,000 nM.

TABLE 1

| Example | rhSYK Activity (nM) |
|---|---|
| 1.1 | A |
| 1.2 | B |
| 1.3 | C |
| 1.4 | A |
| 1.5 | B |
| 1.6 | A |
| 1.7 | B |
| 1.8 | A |
| 1.9 | A |
| 2.1 | C |
| 2.2 | B |
| 2.3 | D |
| 2.4 | D |
| 2.5 | D |
| 2.6 | D |
| 2.7 | C |
| 2.8 | C |
| 2.9 | C |
| 2.10 | D |
| 2.11 | B |
| 2.12 | C |
| 2.13 | B |
| 3.1 | B |
| 3.2 | C |
| 3.3 | B |

Representative compounds of the invention have the $IC_{50}$ values specified in parentheses immediately following the compound number in the above-described assay: 1.1 (3.5 nM), 1.2 (4.5 nM), 1.3 (170 nM), 1.6 (5.8 nM), 2.3 (3500 nM), 2.13 (66 nM), 3.2 (510 nM), and 2.10 (3200 nM).

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:
1. A compound of the Formula (I)

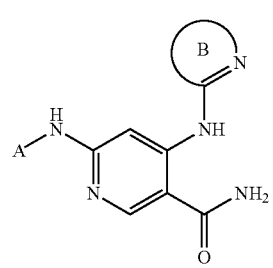

or a pharmaceutically acceptable salt thereof, wherein
B is pyridyl or quinolinyl;
  wherein B is unsubstituted or substituted by 1 to 3 $R^3$ moieties, wherein each $R^3$ moiety is independently selected from the group consisting of $C_1$-$C_3$ alkyl, $C_1$-$C_3$ alkoxy, $C_1$-$C_3$ fluoroalkyl, $C_1$-$C_3$ hydroxyalkyl, halo, hydroxy, amino, ($C_1$-$C_3$ alkyl)amino, di($C_1$-$C_3$ alkyl)amino, and E;
  wherein E is a 5-membered heteroaryl containing 1 to 3 N atoms, wherein E is unsubstituted or substituted by 1 to 2 moieties independently selected from the group consisting of $C_1$-$C_3$ alkyl;
A is selected from the group consisting of:

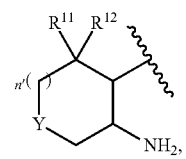

wherein
  Y is —$CH_2$— or —O—;
  $R^{11}$ and $R^{12}$ are independently H or F; and
  n' is 0 or 1; and

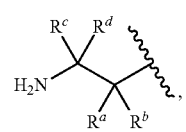

wherein
  $R^a$ and $R^b$ are independently H or $C_1$-$C_6$ alkyl;
  $R^c$ is H, $C_1$-$C_6$ alkyl, $C_1$-$C_3$ fluoroalkyl, $C_3$-$C_6$ cycloalkyl, or —$(CH_2)_r OR^{13}$,
    wherein $R^{13}$ is H or $C_1$-$C_3$ alkyl; and
    r is 1 or 2;
  $R^d$ is H or $C_1$-$C_6$ alkyl,
  or $R^c$ and $R^d$ together with the carbon atom to which they are attached form a group of the formula

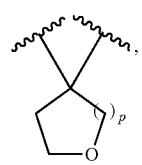

wherein p is 1 or 2.

2. The compound of claim 1 or a pharmaceutically acceptable salt thereof, wherein B is substituted by no more than 2 $R^3$ moieties, and no more than 1 of said $R^3$ moieties is E.

3. The compound of claim 1 or a pharmaceutically acceptable salt thereof, wherein B is substituted by 1 to 3 $R^3$ moieties and one 1 of said $R^3$ moieties is E.

4. The compound of claim 1 or a pharmaceutically acceptable salt thereof, wherein A is

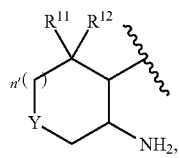

wherein
Y is —$CH_2$— or —O—;
$R^{11}$ and $R^{12}$ are independently H or F; and
n' is 0 or 1.

5. The compound of claim 4, or a pharmaceutically acceptable salt thereof wherein A is selected from the group consisting of

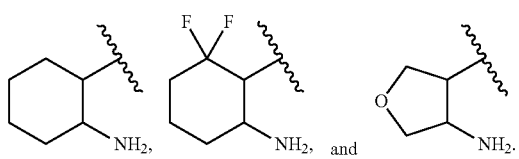

6. The compound of claim 5, or a pharmaceutically acceptable salt thereof wherein A is selected from the group consisting of

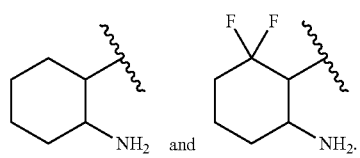 [SMILES: *C1CCCCC1N ; *C1C(N)CCCC1(F)F ; "and"]

7. The compound of claim 1 or a pharmaceutically acceptable salt thereof, wherein A is

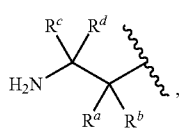

$R^a$ and $R^b$ are independently H or $C_1$-$C_6$ alkyl;
$R^c$ is H, $C_1$-$C_6$ alkyl, $C_1$-$C_3$ fluoroalkyl, $C_3$-$C_6$ cycloalkyl, or —$(CH_2)_r OR^{13}$,
  wherein $R^{13}$ is H or $C_1$-$C_3$ alkyl; and
  r is 1 or 2;
$R^d$ is H or $C_1$-$C_6$ alkyl,
or $R^c$ and $R^d$ together with the carbon atom to which they are attached form a group of the formula

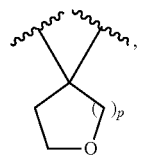

wherein p is 1 or 2.

8. The compound of claim 7 or a pharmaceutically acceptable salt thereof, wherein
$R^a$ and $R^b$ are H;
$R^c$ is H or $C_1$-$C_6$ alkyl; and
$R^d$ is H.

9. The compound of claim 1 having the Formula (IA)

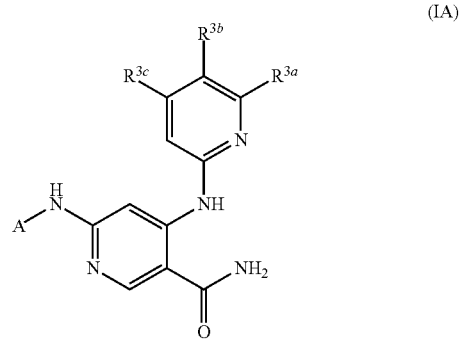

(IA)

or a pharmaceutically acceptable salt thereof, wherein
$R^{3a}$ is halo, $C_1$-$C_3$ alkyl, $C_1$-$C_3$ fluoroalkyl, or a 5-membered heteroaryl containing 1 to 3 N atoms;
  wherein said heteroaryl of $R^{3a}$ is unsubstituted or substituted by 1 to 2 moieties selected from the group consisting of $C_1$-$C_3$ alkyl;
$R^{3b}$ is H, $C_1$-$C_3$ alkyl, halo, or a 5-membered heteroaryl containing 1 to 3 N ring atoms;
  wherein said heteroaryl of $R^{3b}$ is unsubstituted or substituted by 1 to 2 moieties selected from the group consisting of $C_1$-$C_3$ alkyl;
or $R^{3a}$ and $R^{3b}$ together with the carbon atoms to which they are attached form a phenyl ring;
$R^{3c}$ is H, $C_1$-$C_3$ alkyl, halo, or a 5-membered heteroaryl containing 1 to 3 N atoms;
  wherein said heteroaryl of $R^{3c}$ is unsubstituted or substituted by 1 to 2 moieties selected from the group consisting of $C_1$-$C_3$ alkyl;
A is selected from the group consisting of:

(a)

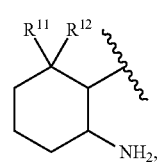

wherein $R^{11}$ and $R^{12}$ are independently H or F; and

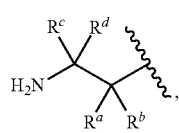
(b)

wherein
$R^a$ and $R^b$ are independently H or $C_1$-$C_6$ alkyl;
$R^c$ is H, $C_1$-$C_6$ alkyl, $C_1$-$C_3$ fluoroalkyl, $C_3$-$C_6$ cycloalkyl, or —$(CH_2)_rOR^{13}$,
wherein $R^{13}$ is H or $C_1$-$C_3$ alkyl; and
r is 1 or 2;
$R^d$ is H or $C_1$-$C_6$ alkyl.

10. The compound of claim 9 or a pharmaceutically acceptable salt thereof, wherein
$R^{3a}$ is $C_1$-$C_3$ alkyl, $C_1$-$C_3$ fluoroalkyl, or a 5-membered heteroaryl containing 1 to 3 N atoms;
wherein said heteroaryl of $R^{3a}$ is unsubstituted or substituted by 1 to 2 moieties selected from the group consisting of $C_1$-$C_3$ alkyl;
$R^{3b}$ is H, $C_1$-$C_3$ alkyl, halo, or a 5-membered heteroaryl containing 1 to 3 N ring atoms;
wherein said heteroaryl of $R^{3b}$ is unsubstituted or substituted by 1 to 2 moieties selected from the group consisting of $C_1$-$C_3$ alkyl;
$R^{3c}$ is H, $C_1$-$C_3$ alkyl, halo, or a 5-membered heteroaryl containing 1 to 3 N atoms;
wherein said heteroaryl of $R^{3c}$ is unsubstituted or substituted by 1 to 2 moieties selected from the group consisting of $C_1$-$C_3$ alkyl.

11. The compound of claim 9 or a pharmaceutically acceptable salt thereof, wherein the moiety

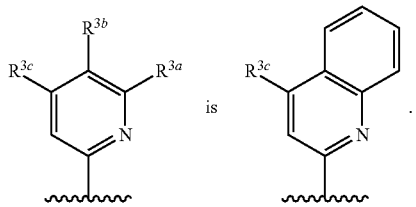

12. The compound of claim 1 or a pharmaceutically acceptable salt thereof, wherein A selected from the group consisting of

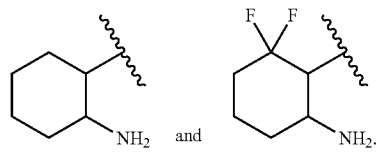 [SMILES: *C1CCCCC1N ; *C1C(N)CCCC1(F)F]

13. The compound of claim 1 or a pharmaceutically acceptable salt thereof, wherein A is wherein

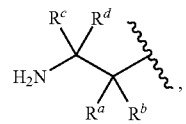

wherein
$R^a$ and $R^b$ are independently H or $C_1$-$C_6$ alkyl;
$R^c$ is H, $C_1$-$C_6$ alkyl, $C_1$-$C_3$ fluoroalkyl, $C_3$-$C_6$ cycloalkyl, or —$(CH_2)_rOR^{13}$,
wherein $R^{13}$ is H or $C_1$-$C_3$ alkyl; and
r is 1 or 2;
$R^d$ is H or $C_1$-$C_6$ alkyl.

14. The compound of claim 13 or a pharmaceutically acceptable salt thereof,
wherein
$R^a$ and $R^b$ are H;
$R^c$ is H or $C_1$-$C_6$ alkyl; and
$R^d$ is H.

15. The compound of claim 1 or a pharmaceutically acceptable salt thereof, wherein the compound is selected from the group consisting of:
rel-6-{[(1R,2S)-2-aminocyclohexyl]amino}-4-[(6-methylpyridin-2-yl)amino]pyridine-3-carboxamide;
6-[(2-aminoethyl)amino]-4-[(6-methylpyridin-2-yl)amino]pyridine-3-carboxamide;
rel-6-{[(1R,2S)-2-aminocyclohexyl]amino}-4-{[6-(2H-1,2,3-triazol-2-yl)pyridin-2-yl]amino}pyridine-3-carboxamide;
rel-6-{[(1R,2S)-2-aminocyclohexyl]amino}-4-[(4,6-dimethylpyridin-2-yl)amino]pyridine-3-carboxamide;
rel-6-{[(1R,2S)-2-aminocyclohexyl]amino}-4-(quinolin-2-ylamino)pyridine-3-carboxamide;
rel-6-{[(1R,2S)-2-aminocyclohexyl]amino}-4-[(5-fluoro-6-methylpyridin-2-yl)amino]pyridine-3-carboxamide;
6-{[2-aminopropyl]amino}-4-{[4,6-bis(1-methyl-1H-pyrazol-4-yl)pyridin-2-yl]amino}pyridine-3-carboxamide;
6-{[2-aminopropyl]amino}-4-{[6-methyl-5-(1-methyl-1-pyrazol-4-yl)pyridin-2-yl]amino}pyridine-3-carboxamide;
rel-6-{[(1R,2S)-2-aminocyclohexyl]amino}-4-{[6-(trifluoromethyl)pyridin-2-yl]amino}pyridine-3-carboxamide;
6-[(2-aminoethyl)amino]-4-[(4,6-dimethylpyridin-2-yl)amino]pyridine-3-carboxamide;
6-[(2-amino-3,3,3-trifluoropropyl)amino]-4-[(4,6-dimethylpyridin-2-yl)amino]pyridine-3-carboxamide;
rel-6-{[(3S,4S)-4-aminotetrahydrofuran-3-yl]amino}-4-[(4,6-dimethylpyridin-2-yl)amino]pyridine-3-carboxamide;
6-{[(4-aminotetrahydro-2H-pyran-4-yl)methyl]amino}-4-[(4,6-dimethylpyridin-2-yl)amino]pyridine-3-carboxamide;
6-{[(3-aminotetrahydrofuran-3-yl)methyl]amino}-4-[(4,6-dimethylpyridin-2-yl)amino]pyridine-3-carboxamide;
6-{[2-amino-3-methoxypropyl]amino}-4-[(6-methylpyridin-2-yl)amino]pyridine-3-carboxamide;
rel-6-{[(1R,2R)-2-aminocyclohexyl]amino}-4-[(6-methylpyridin-2-yl)amino]pyridine-3-carboxamide;
6-[(2-amino-2-methylbutyl)amino]-4-[(6-methylpyridin-2-yl)amino]pyridine-3-carboxamide;
6-[(2-aminobutyl)amino]-4-[(6-methylpyridin-2-yl)amino]pyridine-3-carboxamide;

6-[(2-amino-1-methylethyl)amino]-4-[(4,6-dimethylpyridin-2-yl)amino]pyridine-3-carboxamide;

6-[(2-aminopentyl)amino]-4-[(6-methylpyridin-2-yl)amino]pyridine-3-carboxamide;

6-[(2-amino-2-cyclopropylethyl)amino]-4-[(6-methylpyridin-2-yl)amino]pyridine-3-carboxamide;

6-[(2-aminoethyl)amino]-4-[(5-bromo-6-methylpyridin-2-yl)amino]pyridine-3-carboxamide;

6-{[2-aminopropyl]amino}-4-[(4,6-dimethylpyridin-2-yl)amino]pyridine-3-carboxamide; and rel-6-{[(1S,6S)-6-amino-2,2-difluorocyclohexyl]amino}-4-[(4,6-dimethylpyridin-2-yl)amino]pyridine-3-carboxamide.

16. A pharmaceutical composition comprising a therapeutically effective amount of the compound of claim 1 or a pharmaceutically acceptable salt thereof and a pharmaceutically acceptable carrier.

17. The pharmaceutical composition of claim 16, further comprising an additional therapeutic agent.

\* \* \* \* \*